US010627395B2

(12) United States Patent
Wang et al.

(10) Patent No.: US 10,627,395 B2
(45) Date of Patent: Apr. 21, 2020

(54) METHODS AND SYSTEMS FOR BIOMONITORING

(71) Applicant: Newomics Inc., Emeryville, CA (US)

(72) Inventors: Daojing Wang, Moraga, CA (US); Pan Mao, Milpitas, CA (US)

(73) Assignee: NEWOMICS INC., Berkeley, CA (US)

( * ) Notice: Subject to any disclaimer, the term of this patent is extended or adjusted under 35 U.S.C. 154(b) by 260 days.

(21) Appl. No.: 15/786,949

(22) Filed: Oct. 18, 2017

(65) Prior Publication Data

US 2018/0038850 A1 Feb. 8, 2018

Related U.S. Application Data

(63) Continuation of application No. PCT/US2016/032544, filed on May 13, 2016.

(Continued)

(51) Int. Cl.
*G01N 33/53* (2006.01)
*G01N 33/48* (2006.01)
*G01N 33/50* (2006.01)
*G01N 30/46* (2006.01)
*B01L 3/00* (2006.01)
(Continued)

(52) U.S. Cl.
CPC .... *G01N 33/5308* (2013.01); *B01L 3/502715* (2013.01); *B01L 3/502738* (2013.01); *B01L 3/502753* (2013.01); *B01L 3/502784* (2013.01); *G01N 30/463* (2013.01); *G01N 30/6095* (2013.01); *G01N 30/7266* (2013.01); *G01N 30/88* (2013.01); *G01N 33/48* (2013.01); *G01N 33/50* (2013.01); *G01N 33/5038* (2013.01); *B01L 2200/0647* (2013.01); *B01L 2300/023* (2013.01); *B01L 2300/024* (2013.01); *B01L 2300/0645* (2013.01); *B01L 2300/0816* (2013.01); *B01L 2400/0421* (2013.01); *B01L 2400/0424* (2013.01); *B01L 2400/0622* (2013.01); *G01N 33/57488* (2013.01); *G01N 2030/8813* (2013.01)

(58) Field of Classification Search
None
See application file for complete search history.

(56) References Cited

U.S. PATENT DOCUMENTS 7,906,758 B2 3/2011 Stults et al.
8,022,361 B2 9/2011 Wang et al.
(Continued)

FOREIGN PATENT DOCUMENTS

WO WO-2014093080 A1 6/2014
WO WO-2015112429 A1 7/2015
WO WO-2016183521 A1 11/2016

OTHER PUBLICATIONS

International Search Report dated Aug. 19, 2016 for International Application No. PCT/US2016/032544.
(Continued)

*Primary Examiner* — Xiaoyun R Xu
(74) *Attorney, Agent, or Firm* — Wilson Sonsini Goodrich & Rosati

(57) ABSTRACT

The present disclosure provides methods and systems for detecting a presence or absence of one or more analytes in small volumes of samples. The detected presence or absence of the one or more analytes can be used for a variety of applications including biomonitoring.

24 Claims, 7 Drawing Sheets

Related U.S. Application Data

(60) Provisional application No. 62/160,872, filed on May 13, 2015.

(51) Int. Cl.
    *G01N 30/88*     (2006.01)
    *G01N 30/60*     (2006.01)
    *G01N 30/72*     (2006.01)
    *G01N 33/574*     (2006.01)

(56) References Cited

U.S. PATENT DOCUMENTS

| | | | |
|---|---|---|---|
| 9,518,963 | B2 | 12/2016 | Prentice et al. |
| 9,793,477 | B2 | 10/2017 | Wang et al. |
| 1,033,807 | A1 | 7/2019 | Wang et al. |
| 2003/0027347 | A1* | 2/2003 | Shapiro ............... G01N 33/721 436/66 |
| 2004/0113068 | A1 | 6/2004 | Bousse et al. |
| 2011/0250618 | A1 | 10/2011 | Nelson et al. |
| 2011/0256580 | A1 | 10/2011 | Kim et al. |
| 2014/0110661 | A1 | 4/2014 | Wang et al. |
| 2014/0322723 | A1 | 10/2014 | Halperin et al. |
| 2015/0293063 | A1 | 10/2015 | Wang et al. |
| 2017/0003294 | A1 | 1/2017 | Wang et al. |

OTHER PUBLICATIONS

Mao, et al., Biomonitoring of Perfluorinated Compounds in a Drop of Blood. Environ. Sci. Technol., 2015, 49 (11), pp. 6808-6814.

Mao, et al. Multinozzle emitter array chips for small-volume proteomics. Anal Chem. Jan. 15, 2013;85(2):816-9. doi: 10.1021/ac3032965. Epub Dec. 21, 2012.

Mao, et al. Top-down proteomics of a drop of blood for diabetes monitoring. J Proteome Res. Mar. 7, 2014;13(3):1560-9. doi: 10.1021/pr401074t. Epub Feb. 17, 2014.

Chen, et al. Qualitative and quantitative analysis of tumor cell metabolism via stable isotope labeling assisted microfluidic chip electrospray ionization mass spectrometry. Anal Chem. Feb. 7, 2012;84(3):1695-701. doi: 10.1021/ac300003k. Epub Jan. 24, 2012.

Gao, et al. Characterization of drug permeability in Caco-2 monolayers by mass spectrometry on a membrane-based microfluidic device. Lab Chip. Mar. 7, 2013;13(5):978-85. doi: 10.1039/c2lc41215b. Epub Jan. 23, 2013.

Gasilova, et al. Microchip emitter for solid-phase extraction-gradient elution-mass spectrometry. Anal Chem. Jul. 2, 2013;85(13):6254-63. doi: 10.1021/ac400171e. Epub Jun. 18, 2013.

Han, et al. Binding of perfluorooctanoic acid to rat and human plasma proteins. Chem Res Toxicol. Jun. 2003;16(6):775-81.

International search report and written opinion dated Apr. 24, 2015 for PCT/US2015/011643.

Jung, et al. Microchip electrospray: improvements in spray and signal stability during gradient elution by an inverted postcolumn makeup flow. Anal Chem. Dec. 1, 2011;83(23):9167-73. doi: 10.1021/ac202413z. Epub Nov. 9, 2011.

Kim, et al. Microfabricated monolithic multinozzle emitters for nanoelectrospray mass spectrometry. Anal Chem. May 15, 2007;79(10):3703-7. Epub Apr. 20, 2007.

Kuklenyik, et al. Automated solid-phase extraction and measurement of perfluorinated organic acids and amides in human serum and milk. Environ Sci Technol. Jul. 1, 2004;38(13):3698-704.

Kuklenyik, et al. Measurement of 18 perfluorinated organic acids and amides in human serum using on-line solid-phase extraction. Anal Chem. Sep. 15, 2005;77(18):6085-91.

Lau, et al. Perfluoroalkyl acids: a review of monitoring and toxicological findings. Toxicol Sci. Oct. 2007;99(2):366-94. Epub May 22, 2007.

Lee, et al. Microfluidic mixing: a review. Int J Mol Sci. 2011;12(5):3263-87. doi: 10.3390/ijms12053263. Epub May 18, 2011.

Li, et al. Profiling Cys34 adducts of human serum albumin by fixed-step selected reaction monitoring. Mol Cell Proteomics. Mar. 2011;10(3):M110.004606. doi: 10.1074/mcp.M110.004606. Epub Dec. 30, 2010.

Malinsky, et al. Determination of perfluorinated compounds in fish fillet homogenates: method validation and application to fillet homogenates from the Mississippi River. Anal Chim Acta. Jan. 10, 2011;683(2):248-57. doi: 10.1016/j.aca.2010.10.028. Epub Nov. 3, 2010.

Mao, et al. Multinozzle emitter arrays for nanoelectrospray mass spectrometry. Anal Chem. Aug. 1, 2011;83(15):6082-9. doi: 10.1021/ac2011813. Epub Jul. 5, 2011.

Mao, et al. Strategy for signaling molecule detection by using an integrated microfluidic device coupled with mass spectrometry to study cell-to-cell communication. Anal Chem. Jan. 15, 2013;85(2):868-76. doi: 10.1021/ac303164b. Epub Dec. 31, 2012.

Nakamura, et al. The endogenous exposome. DNA Repair (Amst). Jul. 2014;19:3-13. doi: 10.1016/j.dnarep.2014.03.031. Epub Apr. 24, 2014.

Ouyang, et al. Nondestructive sampling of living systems using in vivo solid-phase microextraction. Chem Rev. Apr. 13, 2011;111(4):2784-814. doi: 10.1021/cr100203t. Epub Jan. 27, 2011.

Phinney, et al. An, et al. Development of a Standard Reference Material for metabolomics research. Anal Chem. Dec. 17, 2013;85(24):11732-8. doi: 10.1021/ac402689t. Epub Dec. 3, 2013.

Rappaport, et al. Adductomics: characterizing exposures to reactive electrophiles. Toxicol Lett. Aug. 13, 2012;213(1):83-90. doi: 10.1016/j.toxlet.2011.04.002. Epub Apr. 8, 2011.

Rappaport, et al. The blood exposome and its role in discovering causes of disease. Environ Health Perspect. Aug. 2014;122(8):769-74. doi: 10.1289/ehp.1308015. Epub Mar. 21, 2014.

Reiner, et al. Determination of perfluorinated compounds in human plasma and serum Standard Reference Materials using independent analytical methods. Anal Bioanal Chem. Nov. 2011;401(9):2899-907. doi: 10.1007/s00216-011-5380-x. Epub Sep. 9, 2011.

Renner. Growing concern over perfluorinated chemicals. Environ Sci Technol. Apr. 1, 2001;35(7):154A-160A.

Vuckovic, et al. Solid-phase microextraction in bioanalysis: New devices and directions. J Chromatogr A. Jun. 18, 2010;1217(25):4041-60. doi: 10.1016/j.chroma.2009.11.061. Epub Dec. 4, 2009.

Wang, et al. Single cell analysis: the new frontier in 'omics'. Trends Biotechnol. Jun. 2010;28(6):281-90. doi: 10.1016/j.tibtech.2010.03.002. Epub Apr. 29, 2010.

Yang, et al. Coupling on-chip solid-phase extraction to electrospray mass spectrometry through an integrated electrospray tip. Electrophoresis. Oct. 2005;26(19):3622-30.

Ying, et al. Microfluidic chip-based technologies: emerging platforms for cancer diagnosis. BMC Biotechnol. Sep. 27, 2013;13:76. doi: 10.1186/1472-6750-13-76.

Yu, et al. Monolithic porous polymer for on-chip solid-phase extraction and preconcentration prepared by photoinitiated in situ polymerization within a microfluidic device. Anal Chem. Nov. 1, 2001;73(21):5088-96.

Fortier, et al. Integrated microfluidic device for mass spectrometry-based proteomics and its application to biomarker discovery programs. Anal Chem. Mar. 15, 2005; 77(6):1631-40.

U.S. Appl. No. 15/203,666 Office Action dated Sep. 18, 2018.

Chen, et al. Quantitation of Intact Proteins in Human Plasma Using Top-Down Parallel Reaction Monitoring—MS. Anal Chem. Sep. 18, 2018;90(18):10650-10653. doi: 10.1021/acs.analchem.8b02699. Epub Sep. 7, 2018.

U.S. Appl. No. 15/203,666 Office Action dated Feb. 8, 2019.

U.S. Appl. No. 15/203,666 Notice of Allowance dated Apr. 19, 2019.

Co-pending U.S. Appl. No. 16/412,039, filed May 14, 2019.

* cited by examiner

Chip assembly

Workflow

METHODS AND SYSTEMS FOR BIOMONITORING

CROSS-REFERENCE

This application is a continuation of International Patent Application No. PCT/US2016/032544, filed May 13, 2016, which claims the benefit of U.S. Provisional Patent Application No. 62/160,872, filed May 13, 2015, each of which is incorporated herein by reference in its entirety.

STATEMENT OF GOVERNMENT SUPPORT

This invention was made with government support under grant numbers ES022360, ES023529, GM109682, AT008297, AG046025, and AI106100 and contract number HHSN261201300033C awarded by the National Institutes of Health. The government has certain rights in the invention.

BACKGROUND

Compared to the traditional exposure assessment using ambient monitoring of environmental pollutants, rapid and sensitive detection of large sets of analytes including exogenous chemicals, their metabolites, and other derivatives such as protein adducts ("exposome", e.g., metabolome and adductome) using human specimens such as blood and urine, which reflect the complexity of exposure in the personal environment, has opened up new opportunities for epidemiologic studies of human exposure. However, two key challenges remain for "exposomics": (1) rapid and efficient processing of small volumes of biospecimens, especially human blood samples; and (2) detecting multiple and/or multiclass analytes simultaneously with high-sensitivity and high-specificity from such small volumes of biospecimens.

So far, there have been a few methods that have been adopted to directly couple sample processing (e.g., solid-phase extraction (SPE)) with nanoflow liquid chromatography-mass spectrometry (LC-MS) in order to minimize sample loss and increase detection sensitivity. However, these methods usually require substantially large sample volumes for analyzing low concentrations of target analytes, which makes the methods impractical for, e.g., population studies of multiple (multiclass) analytes where only small volumes of samples are collected. Accordingly, there is a need for a platform that may enable sensitive, robust, high-throughput and multiplexed biomonitoring using small volumes of samples.

SUMMARY

Recognized herein are various issues with systems and methods currently available for biomonitoring. For instance, in conventional SPE-LC-MS systems, SPE is generally on-line coupled with high-flow LC-MS because large SPE column volume is required for efficient extraction of target analytes from complex biological samples. Such requirement makes the SPE incompatible with nanoflow LC-MS and may result in substantial peak broadening and poor chromatographic separation due to the volume mismatch. Therefore, there is a need for microfluidic devices which include a monolithic interface between SPE and nanoLC-MS. Such microfluidic device may substantially improve the ability of a variety of sample testing and measurement techniques such as biomonitoring which includes monitoring bioaccumulation of chemicals from small sample volumes.

The present disclosure provides methods and system for detecting a presence or absence of one or more analytes in small volumes of samples obtained from a subject. The presence or absence of the one or more analytes may be used for identifying a biological state or condition of the subject. The detection of the presence or absence of the analytes may further comprise determining certain levels of the analytes, for example, concentrations, quantities of the analytes. The determined levels of the analytes may be employed for applications such as biomonitoring including, e.g., monitoring toxic chemical compounds, elements, or their metabolites in biological substances with small sample volumes. Methods and systems provided herein may enable high-sensitivity, specificity and/or throughput, multiplexed, and multi-analyte biomonitoring using small volumes of samples such as biospecimens.

An aspect of the present disclosure provides a method for detecting a presence of a plurality of analytes in a biological sample of a subject, comprising: (a) providing a microfluidic device comprising (i) a first fluid channel including a first separation medium that is adapted to extract the plurality of analytes from the biological sample; (ii) a second fluid channel in fluid communication with the first fluid channel, wherein the second fluid channel includes a second separation medium that is adapted to separate the plurality of analytes extracted in the first separation medium into subsets of analytes along the second fluid channel; and (iii) at least one emitter in fluid communication with the second fluid channel, wherein the at least one emitter comprises at least one nozzle that is operatively coupled to a detector, which detector is adapted to generate signals that are indicative of each of the subsets of analytes; (b) directing the biological sample through the first fluid channel to extract the plurality of analytes from the biological sample; (c) directing the plurality of analytes extracted in the first fluid channel to the second fluid channel to separate the plurality of analytes extracted in the first separation channel into the subsets of analytes along the second fluid channel; and (d) directing the subsets of analytes from the second fluid channel through the at least one nozzle of the at least one emitter to the detector, wherein the detector generates signals upon exposure to the subsets of analytes, which signals are indicative of a presence of each of the subsets of analytes in the biological sample.

In some embodiments of aspects provided herein, the microfluidic device is part of a disposable chip. In some embodiments of aspects provided herein, the microfluidic device is separate from the detector. In some embodiments of aspects provided herein, the at least one emitter comprises a plurality of emitters. In some embodiments of aspects provided herein, the at least one nozzle extends from a base tube that is in fluid communication with the second fluid channel, and the base tube has a larger cross-sectional dimension than the at least one nozzle. In some embodiments of aspects provided herein, the at least one nozzle is a nanotube or microtube. In some embodiments of aspects provided herein, the at least one nozzle and the base tube are monolithic. In some embodiments of aspects provided herein, the at least one nozzle has a cross-sectional dimension that is less than or equal to about 50 micrometers. In some embodiments of aspects provided herein, the cross-sectional dimension is less than or equal to about 25 micrometers. In some embodiments of aspects provided herein, the cross-sectional dimension is less than or equal to about 10 micrometers. In some embodiments of aspects provided herein, the at least one nozzle comprises a plurality of nozzles. In some embodiments of aspects provided herein, the microfluidic device comprises a first substrate adjacent to a second substrate, and the at least one emitter is disposed between the first substrate and the second substrate. In some embodiments of aspects provided herein, the first substrate is formed of silicon. In some embodiments of aspects provided herein, the second substrate is formed of silicon oxide. In some embodiments of aspects provided herein, the first separation medium and the second separation medium are different. In some embodiments of aspects provided herein, the first separation medium and the second separation medium are the same. In some embodiments of aspects provided herein, the first separation medium and the second separation medium comprise solid materials. In some embodiments of aspects provided herein, the first separation medium and the second separation medium comprise beads and/or monolithic porous structures. In some embodiments of aspects provided herein, the beads have a cross-sectional dimension from about 1 micrometer to 50 micrometers. In some embodiments of aspects provided herein, each of the beads has a plurality of pores. In some embodiments of aspects provided herein, each of the plurality of pores has a pore size from about 1 nanometer to about 30 nanometers.

In some embodiments of aspects provided herein, the detector is a mass spectrometer. In some embodiments of aspects provided herein, the subsets of analytes are detected based on an ionization pattern of the subsets in the mass spectrometer. In some embodiments of aspects provided herein, the mass spectrometer is selected from the group consisting of an Orbitrap mass spectrometer, a triple-quadrupole mass spectrometer, and a time-of-flight mass spectrometer. In some embodiments of aspects provided herein, the detector is any detector other than a mass spectrometer. In some embodiments of aspects provided herein, the first fluid channel is configured to perform solid-phase extraction (SPE) on the biological sample. In some embodiments of aspects provided herein, the microfluidic device further comprises a third fluid channel between and in fluid communication with the first fluid channel and the second fluid channel, and the third fluid channel facilitates mixing of the plurality of analytes from the first fluid channel. In some embodiments of aspects provided herein, the third fluid channel includes a barrier structure, wherein a cross-section of the barrier structure is less than a height of the third fluid channel. In some embodiments of aspects provided herein, the barrier structure comprises periodic structures. In some embodiments of aspects provided herein, the barrier structure comprises staggered herringbone grooves. In some embodiments of aspects provided herein, the method further comprises generating an electronic report that is indicative of the presence of the plurality of analytes in the biological sample. In some embodiments of aspects provided herein, the electronic report identifies a presence of a biological state or condition of the subject based on the presence of the plurality of analytes in the biological sample. In some embodiments of aspects provided herein, the method further comprises providing the electronic report for display on a user interface of an electronic device of a user. In some embodiments of aspects provided herein, the user is the subject. In some embodiments of aspects provided herein, the user is a healthcare provider of the subject. In some embodiments of aspects provided herein, the method further comprises identifying a biological state or condition of the subject based on the presence of the plurality of analytes in the biological sample. In some embodiments of aspects provided herein, the biological state or condition is selected from a group consisting of a disease, a disorder, a non-disease condition, and a therapeutic response to drug treatments or other therapies. In some embodiments of aspects provided herein, the method further comprises detecting the presence of the subsets of analytes at multiple time points to monitor a progression of the biological state or condition in the subject. In some embodiments of aspects provided herein, the method further comprises determining a concentration and/or relative amount of each of the subsets of analytes in the biological sample. In some embodiments of aspects provided herein, the concentration and/or relative amount of each of the subsets of analytes in the biological sample is associated with a biological state or condition of the subject. In some embodiments of aspects provided herein, the plurality of analytes comprises chemicals, lipids, glycans, proteins, peptides, and/or nucleic acids. In some embodiments of aspects provided herein, the plurality of analytes comprises perfluorinated compounds (PFCs) and other environmental toxins. In some embodiments of aspects provided herein, the biological sample is a blood sample. In some embodiments of aspects provided herein, the blood sample is a whole blood sample. In some embodiments of aspects provided herein, the blood sample is a plasma sample. In some embodiments of aspects provided herein, the blood sample is a serum sample. In some embodiments of aspects provided herein, the biological sample has volume less than or equal to about 50 microliters. In some embodiments of aspects provided herein, the volume is less than or equal to about 40 microliters. In some embodiments of aspects provided herein, the volume is less than or equal to about 30 microliters. In some embodiments of aspects provided herein, the volume is less than or equal to about 20 microliters. In some embodiments of aspects provided herein, the volume is less than or equal to about 10 microliters. In some embodiments of aspects provided herein, the volume is less than or equal to about 5 microliters. In some embodiments of aspects provided herein, the volume is less than or equal to about 1 microliter. In some embodiments of aspects provided herein, each of the subsets of analytes includes an individual analyte among the plurality of analytes. In some embodiments of aspects provided herein, (b)-(d) are performed in a time period that is less than or equal to 2 hours. In some embodiments of aspects provided herein, the time period is less than or equal to 1 hour. In some embodiments of aspects provided herein, the time period is less than or equal to 30 minutes. In some embodiments of aspects provided herein, the subsets of analytes are detected at a specificity (or precision) of at least about 80%. In some embodiments of aspects provided herein, the specificity is at least about 90%. In some embodiments of aspects provided herein, the specificity is at least about 95%. In some embodiments of aspects provided herein, the specificity is at least about 99%. In some embodiments of aspects provided herein, the subsets of analytes are detected at a sensitivity (or accuracy) of at least about 80%. In some embodiments of aspects provided herein, the sensitivity is at least about 90%. In some embodiments of aspects provided herein, the sensitivity is at least about 95%. In some embodiments of aspects provided herein, the sensitivity is at least about 99%. In some embodiments of aspects provided herein, the subsets of analytes are detected at a detection limit of less than or equal to about 1 nanogram/milliliter (ng/mL).

Another aspect of the present disclosure provides a system for detecting a presence of a plurality of analytes in a biological sample of a subject, comprising: a microfluidic device comprising (i) a first fluid channel including a first separation medium that is adapted to extract the plurality of analytes from the biological sample; (ii) a second fluid channel in fluid communication with the first fluid channel, wherein the second fluid channel includes a second separation medium that is adapted to separate the plurality of analytes extracted in the first separation medium into subsets of analytes along the second fluid channel; and (iii) at least one emitter in fluid communication with the second fluid channel, wherein the at least one emitter comprises at least one nozzle; a detector operatively coupled to the at least one emitter, wherein the detector is adapted to generate signals that are indicative of each of the subsets of analytes; and one or more computer processors operatively coupled to the microfluidic device, wherein the one or more computer processors are individually or collectively programmed to (1) direct the biological sample through the first fluid channel to extract the plurality of analytes from the biological sample; (2) direct the plurality of analytes extracted in the first fluid channel to the second fluid channel to separate the plurality of analytes extracted in the first separation channel into the subsets of analytes along the second fluid channel; and (3) direct the subsets of analytes from the second fluid channel through the at least one nozzle of the at least one emitter to the detector, wherein the detector generates signals upon exposure to the subsets of analytes, which signals are indicative of a presence of each of the subsets of analytes in the biological sample.

In some embodiments of aspects provided herein, the microfluidic device is a multiplex chip. In some embodiments of aspects provided herein, the multiplex chip is fabricated as a monolithic unit. In some embodiments of aspects provided herein, the multiplex chip is assembled using parallel 1-plex units. In some embodiments of aspects provided herein, the microfluidic device comprises a first substrate adjacent to a second substrate, and the at least one emitter is disposed between the first substrate and the second substrate. In some embodiments of aspects provided herein, the first fluid channel and the second fluid channel are disposed between the first substrate and the second substrate. In some embodiments of aspects provided herein, the first substrate includes a plurality of semiconductor layers. In some embodiments of aspects provided herein, the one or more computer processors are individually or collectively programmed to identify a biological state or condition of the subject based on the presence of the plurality of analytes in the biological sample. In some embodiments of aspects provided herein, the one or more computer processors are individually or collectively programmed to detect the subsets of analytes at multiple time points to monitor a progression of the biological state or condition of the subject. In some embodiments of aspects provided herein, the one or more computer processors are individually or collectively to generate an electronic report that is indicative of the presence of the plurality of analytes in the biological sample. In some embodiments of aspects provided herein, the one or more computer processors are individually or collectively programmed to provide the electronic report for display on a user interface of an electronic device of a user. In some embodiments of aspects provided herein, the one or more computer processors are individually or collectively programmed to determine a concentration and/or relative amount of each of the subsets of analytes. In some embodiments of aspects provided herein, the one or more computer processors are individually or collectively programed to perform (1)-(3) in a time period that is less than or equal to 2 hours. In some embodiments of aspects provided herein, the time period is less than or equal to 1 hour. In some embodiments of aspects provided herein, the at least one emitter comprises a plurality of emitters. In some embodiments of aspects provided herein, the at least one nozzle comprises a plurality of nozzles. In some embodiments of aspects provided herein, the microfluidic device further comprises a third fluid channel between and in fluid communication with the first fluid channel and the second fluid channel, wherein the third fluid channel facilitates mixing of the plurality of analytes from the first fluid channel. In some embodiments of aspects provided herein, the third fluid channel includes a barrier structure, wherein a cross-section of the barrier structure is less than a height of the third fluid channel. In some embodiments of aspects provided herein, the barrier structure comprises periodic structures. In some embodiments of aspects provided herein, the barrier structure comprises staggered herringbone grooves. In some embodiments of aspects provided herein, the second fluid channel comprises an enrichment channel and a separation channel downstream of the enrichment channel. In some embodiments of aspects provided herein, the enrichment channel is adapted to purify and/or concentrate the plurality of analytes extracted in the first fluid channel as they move along the enrichment channel. In some embodiments of aspects provided herein, the separation channel is adapted to separate the plurality of analytes into the subsets of analytes. In some embodiments of aspects provided herein, the microfluidic device comprises at least one fluid port in fluid communication with the first fluid channel, which the at least one fluid port is adapted to receive the biological sample and direct the biological sample to the first fluid channel. In some embodiments of aspects provided herein, the microfluidic device comprises a plurality of fluid ports, each in fluid communication with at least one of the first fluid channel, the second fluid channel and the third fluid channel. In some embodiments of aspects provided herein, the microfluidic device further comprises at least one valve in fluid communication with the plurality of fluid ports, wherein the at least one valve is configured to define flow paths on the microfluidic device. In some embodiments of aspects provided herein, the at least one valve comprises a plurality of valves. In some embodiments of aspects provided herein, the plurality of valves comprises switching valves. In some embodiments of aspects provided herein, the one or more computer processors are individually or collectively programmed to identify the subsets of analytes based on the signals from the detector.

Another aspect of the present disclosure provides a method for detecting a presence of a plurality of analytes in a biological sample of a subject, comprising: providing a microfluidic device including at least one fluid channel in fluid communication with at least one emitter having at least one nozzle that is operatively coupled to a detector, wherein the fluid channel includes a separation medium that is adapted to separate the plurality of analytes into subsets of analytes along the fluid channel, and wherein the detector is adapted to generate signals upon exposure to the subsets of analytes, which signals are indicative of each of the subsets of analytes; directing the biological sample having a volume less than or equal to about 50 microliters to the fluid channel under conditions that permit the plurality of analytes to be separated into the subsets of analytes along the fluid channel, wherein the biological sample is directed to the fluid channel without any processing or treatment; directing the subsets of analytes from the fluid channel to the at least one nozzle; and directing the subsets of analytes from the at least one nozzle to the detector to detect the presence of the subsets of analytes in the biological sample based on the signals generated by the detector.

In some embodiments of aspects provided herein, the microfluidic device is part of a disposable chip. In some embodiments of aspects provided herein, the microfluidic device is separate from the detector. In some embodiments of aspects provided herein, the at least one emitter comprises a plurality of emitters. In some embodiments of aspects provided herein, the at least one nozzle extends from a base tube that is in fluid communication with the at least one fluid channel, and the base tube has a larger cross-sectional dimension than the at least one nozzle. In some embodiments of aspects provided herein, the at least one nozzle and the base tube are monolithic. In some embodiments of aspects provided herein, the at least one nozzle has a cross-sectional dimension less than or equal to about 50 micrometers. In some embodiments of aspects provided herein, the at least one nozzle comprises a plurality of nozzles. In some embodiments of aspects provided herein, the microfluidic device comprises a first substrate adjacent to a second substrate, and the at least one emitter is disposed between the first substrate and the second substrate. In some embodiments of aspects provided herein, the separation medium comprises beads and/or monolithic porous structures. In some embodiments of aspects provided herein, the detector is a mass spectrometer. In some embodiments of aspects provided herein, the subsets of analytes are detected based on an ionization pattern of the subsets in the mass spectrometer. In some embodiments of aspects provided herein, the at least one fluid channel comprises a first fluid channel and a second channel in fluid communication with the first fluid channel. In some embodiments of aspects provided herein, the first fluid channel is configured to perform sample processing and/or treatment on the microfluidic device. In some embodiments of aspects provided herein, the first fluid channel comprises an additional separation medium that is adapted to extract the plurality of analytes from the biological sample. In some embodiments of aspects provided herein, the first fluid channel is configured to perform solid-phase extraction (SPE) on the biological sample. In some embodiments of aspects provided herein, the additional separation medium and the separation medium are different. In some embodiments of aspects provided herein, the additional separation medium and the separation medium are the same. In some embodiments of aspects provided herein, the second fluid channel further comprises an enrichment channel and a separation channel downstream of the enrichment channel, wherein the enrichment channel is adapted to purify and/or concentrate the plurality of analytes extracted in the first fluid channel as they move along the enrichment channel, and wherein the separation channel is adapted to separate the plurality of analytes purified and/or concentrated in the enrichment channel into the subsets of analytes along the separation channel. In some embodiments of aspects provided herein, the at least one fluid channel further comprises a third fluid channel between and in fluid communication with the first fluid channel and the second fluid channel, and the third fluid channel facilitates mixing of the plurality of analytes from the first fluid channel. In some embodiments of aspects provided herein, the third fluid channel includes a barrier structure, wherein a cross-section of the barrier structure is less than a height of the third fluid channel. In some embodiments of aspects provided herein, the barrier structure comprises periodic structures. In some embodiments of aspects provided herein, the barrier structure comprises staggered herringbone grooves. In some embodiments of aspects provided herein, the method further comprises generating an electronic report that is indicative of the presence of the plurality of analytes in the biological sample. In some embodiments of aspects provided herein, the method further comprises providing the electronic report for display on a user interface of an electronic device of a user. In some embodiments of aspects provided herein, the method further comprises identifying a biological state or condition of the subject based on the presence of the plurality of analytes in the biological sample. In some embodiments of aspects provided herein, the biological state or condition is selected from a group consisting of a disease, a disorder, a non-disease condition, and a therapeutic response to drug treatments or other therapies. In some embodiments of aspects provided herein, the method further comprises detecting the presence of the subsets of analytes at multiple time points to monitor a progression of the biological state or condition in the subject. In some embodiments of aspects provided herein, the plurality of analytes comprises chemicals, lipids, glycans, proteins, peptides, and/or nucleic acids. In some embodiments of aspects provided herein, the plurality of analytes comprises perfluorinated compounds (PFCs) and other environmental toxins. In some embodiments of aspects provided herein, the biological sample is a blood sample. In some embodiments of aspects provided herein, each of the subsets of analytes includes an individual analyte among the plurality of analytes. In some embodiments of aspects provided herein, (b)-(d) are performed in a time period that is less than or equal to 2 hours. In some embodiments of aspects provided herein, the subsets of analytes are detected at a specificity of at least about 80%. In some embodiments of aspects provided herein, the subsets of analytes are detected at a sensitivity of at least about 80%. In some embodiments of aspects provided herein, the subsets of analytes are detected at a detection limit of less than or equal to about 1 nanogram/milliliter (ng/mL).

Another aspect of the present disclosure provides a system for detecting a presence of a plurality of analytes in a biological sample of a subject, comprising: a microfluidic device comprising at least one fluid channel in fluid communication with at least one emitter having at least one nozzle, wherein the fluid channel includes a separation medium that is adapted to separate the plurality of analytes into subsets of analytes along the fluid channel; a detector operatively coupled to the at least on emitter, wherein the detector is adapted to generate signals upon exposure to the subsets of analytes, which signals are indicative of each of the subsets of analytes; and one or more computer processors operatively coupled to the microfluidic device, wherein the one or more computer processors are individually or collectively programmed to (i) direct the biological sample having a volume less than or equal to about 50 microliters to the fluid channel under conditions that permit the plurality of analytes to be separated into the subsets of analytes along the fluid channel, wherein the biological sample is directed to the fluid channel without any processing or treatment; (ii) direct the subsets of analytes from the fluid channel to the at least one nozzle; and (iii) direct the subsets of analytes from the at least one nozzle to the detector to detect the presence of the subsets of analytes in the biological sample based on the signals generated by the detector.

In some embodiments of aspects provided herein, the microfluidic device is a multiplex chip. In some embodiments of aspects provided herein, the multiplex chip is fabricated as a monolithic unit. In some embodiments of aspects provided herein, the multiplex chip is assembled using parallel 1-plex units. In some embodiments of aspects provided herein, the microfluidic device comprises a first substrate adjacent to a second substrate, and the at least one emitter is disposed between the first substrate and the second substrate. In some embodiments of aspects provided herein, the at least one fluid channel is disposed between the first substrate and the second substrate. In some embodiments of aspects provided herein, the first substrate includes a plurality of semiconductor layers. In some embodiments of aspects provided herein, the one or more computer processors are individually or collectively programmed to identify a biological state or condition of the subject based on the presence of the plurality of analytes in the biological sample. In some embodiments of aspects provided herein, the one or more computer processors are individually or collectively programmed to detect the subsets of analytes at multiple time points to monitor a progression of the biological state or condition of the subject. In some embodiments of aspects provided herein, the one or more computer processors are individually or collectively programmed to generate an electronic report that is indicative of the presence of the plurality of analytes in the biological sample. In some embodiments of aspects provided herein, the one or more computer processors are individually or collectively programed to perform (i)-(iii) in a time period that is less than or equal to 2 hours. In some embodiments of aspects provided herein, the at least one emitter comprises a plurality of emitters. In some embodiments of aspects provided herein, the at least one nozzle comprises a plurality of nozzles. In some embodiments of aspects provided herein, the at least one fluid channel comprises a first fluid channel and a second channel in fluid communication with the first fluid channel. In some embodiments of aspects provided herein, the first fluid channel is configured to perform sample processing and/or treatment on the microfluidic device. In some embodiments of aspects provided herein, the first fluid channel comprises an additional separation medium that is adapted to extract the plurality of analytes from the biological sample. In some embodiments of aspects provided herein, the first fluid channel is configured to perform solid-phase extraction (SPE) on the biological sample. In some embodiments of aspects provided herein, the second fluid channel further comprises an enrichment channel and a separation channel downstream of the enrichment channel. In some embodiments of aspects provided herein, the enrichment channel is adapted to purify and/or concentrate the plurality of analytes extracted in the first fluid channel as they move along the enrichment channel, and the separation channel is adapted to separate the plurality of analytes purified and/or concentrated in the enrichment channel into the subsets of analytes along the separation channel. In some embodiments of aspects provided herein, the at least one fluid channel further comprises a third fluid channel between and in fluid communication with the first fluid channel and the second fluid channel, wherein the third fluid channel facilitates mixing of the plurality of analytes from the first fluid channel. In some embodiments of aspects provided herein, the third fluid channel includes a barrier structure, wherein a cross-section of the barrier structure is less than a height of the third fluid channel. In some embodiments of aspects provided herein, the microfluidic device further comprises at least one fluid port in fluid communication with the first fluid channel, which the at least one fluid port is adapted to receive the biological sample and direct the biological sample to the first fluid channel. In some embodiments of aspects provided herein, the microfluidic device comprises a plurality of fluid ports, each in fluid communication with at least one of the first fluid channel, the second fluid channel and the third fluid channel. In some embodiments of aspects provided herein, the microfluidic device further comprises at least one valve in fluid communication with the plurality of fluid ports, wherein the at least one valve is configured to define flow paths on the microfluidic device. In some embodiments of aspects provided herein, the at least one valve comprises a plurality of valves. In some embodiments of aspects provided herein, the plurality of valves comprises switching valves. In some embodiments of aspects provided herein, the one or more computer processors are individually or collectively programmed to identify the subsets of analytes based on the signals from the detector.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 1A shows functional modules on the chip including a solid phase extraction (SPE) column, a herringbone mixer, a trap column, a liquid chromatography column, an emitter, and multiple inlet/outlet holes (i), and the zoom-in view of the mixer (ii) comprising herringbone grooves. FIG. 1B shows high-resolution photographs of the chip and its assembly with a custom-built manifold and fittings, relative to a US penny. FIG. 1C shows an example workflow for on-chip and online SPE-nanoLC-MS analysis of PFCs in small volumes of human plasma. The flow direction for each major step is specified with fluidic inlet and outlet port positions. The connection between the SPE column and trap column includes a herringbone mixer for efficient solvent mixing before the mixers to allow for the titration of organic content to avoid solvent incompatibility between different columns. A makeup-flow channel between the exit of LC column and the emitter is employed to improve spray and signal stability;

FIG. 4A shows response of PFHxS, $^{18}O_2$-PFHxS, and $^{13}C_4$-PFOA using $^{13}C_8$-PFOA as the internal standard. FIG. 4B shows response of $^{13}C_5$-PFNA, PFOS, $^{13}C_4$-PFOS, PFDeA, $^{13}C_2$-PFDeA, $^{13}C_2$-PFUnA, $^{13}C_2$-PFDoA, and PFOSA using $^{13}C_8$-PFOS as the internal standard;

In FIG. 5A, sample recovery rate is obtained for 1 microliter of pooled human plasma spiked with PFCs of 25 pg each. Error bars, s.d. (n≥3). In FIG. 5B, limit of detection (LOD) of PFCs is measured as the smallest total amount (fg) and the lowest concentration (ng/ml) achieving a S/N of 3.

DETAILED DESCRIPTION

Figure 1A:
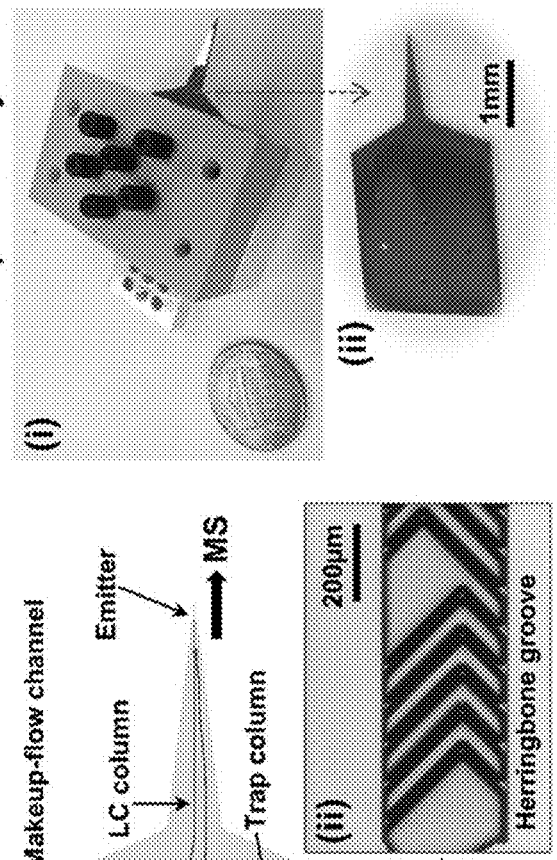
FIGS. 1A-1C show an example silicon microfluidic chip for biomonitoring.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular forms "a", "an", and "the" include plural references unless the context clearly dictates otherwise.

As used herein, the term "subject" generally refers to any living being comprised of at least one cell. A subject may be a single cell organism or a multi-cellular organism, such as a mammal, a non-mammal (e.g., a bird), or a plant (e.g., a tree). An organism may be a mammal, such as, for example, a human or an animal such as a primate (e.g., a monkey, chimpanzee, etc.), a domesticated animal (e.g., a dog, cat, etc.), farm animal (e.g., goat, sheep, pig, cattle, horse, etc.), or laboratory animal (e.g., mouse, rat, etc.). A subject may be a patient. A subject may be an individual that has or is suspected of having a disease.

Examples of subjects may include, but not limited to, humans, mammals, non-human mammals, rodents, amphibians, reptiles, mayines, felines, bovines, equines, goats, ovines, hens, avines, mice, rabbits, insects, slugs, microbes, bacteria, parasites, or fish. In some cases, the subject may be a patient who is having, suspected of having, or at a risk of developing a disease or disorder. In some cases, the subject may be a pregnant woman. The subject may be a normal healthy pregnant woman, or a pregnant woman who is at risk of carrying a baby with certain birth defect.

Overview

The present disclosure provides methods and systems for detecting a presence or absence of one or more analytes in a sample. The presence or absence of the one or more analytes in the sample may be indicative of or associated with a biological state or condition of a subject. Examples of such biological state or condition include, without limitation, a contamination, a disease, a disorder, a non-disease condition, or therapeutic responses to different drug treatments and/or other therapies. The presence or absence of the one or more analytes may also be used for determining a risk of developing a disease, diagnosing a disease or monitoring a progression of a disease in a subject. In some cases, the presence or absence of the one or more analytes may further comprise determining a level including, e.g., a concentration, a quantity and/or an amount of the analytes. The determined level of the analytes may then be utilized to draw a conclusion. In some cases, the determined level of the analytes in the sample may or may not be compared with that in a control sample prior to a conclusion. For example, in some cases, an elevated or lowered amount of the analytes in the sample of a subject may be indicative of a specific biological state or condition. While in some cases, when compared with the control, the same level of one or more substances in the sample of a subject may signal the absence of a biological state or condition.

The systems provided herein may comprise (1) a microfluidic device comprising at least one fluid channel, and at least one emitter in fluid communication with the at least one fluid channel; (2) a detection module comprising at least one detector operatively coupled to the at least one emitter; and (3) a computer control system which controls the operation of the microfluidic device (e.g., fluid flow, voltage, heating etc.) and/or the detection module.

The microfluidic device may comprise a plurality of fluid channels. The plurality of fluid channels may be in fluid communication with one another. Each of the fluid channels may be configured or adapted to perform the same or different functions or procedures, including, e.g., sample processing and/or treatment, analyte purification, concentration and/or separation. Each of the fluid channels may or may not comprise a separation medium, which is adapted to facilitate or perform a specific function or procedure. In some cases, only a certain percentage of the fluid channels comprise a separation medium, for example, at least about 1%, 5%, 10%, 20%, 25%, 30%, 35%, 40%, 45%, 50%, 55%, 60%, 65%, 70%, 75%, 80%, 85%, 90%, 95%, or 99% of the fluid channels may comprise a separation medium. Each fluid channel may or may not comprise the same separation medium. In some cases, each fluid channel comprises a different separation medium. In some cases, all of the fluid channels comprise the same separation medium. In some cases, at least about 1%, 5%, 10%, 20%, 25%, 30%, 35%, 40%, 45%, 50%, 55%, 60%, 65%, 70%, 75%, 80%, 85%, 90%, 95% or more of the fluid channels comprise the same separation medium.

The separation medium may be polar or non-polar. The separation medium may be hydrophilic, hydrophobic, or amphiphilic. The separation medium may be adapted to facilitate or enable certain interactions between the separation medium and the sample (and/or analytes). Such interactions may comprise polar interactions, ionic interactions, or interactions based on molecular size.

The at least one emitter may include a plurality of emitters, such as at least about 2, 3, 4, 5, 6, 7, 8, 9, 10, 20, 30, 40, or 50 or more emitters. Each emitter may comprise at least one nozzle. In some cases, the at least one nozzle includes a plurality of nozzles, such as at least about 2, 3, 4, 5, 6, 7, 8, 9, 10, 20, 30, 40, 50, 100 or more nozzles per emitter.

The computer control system may comprise one or more computer processors which are operatively coupled to the detection module and/or the microfluidic device. The one or more computer processors may be individually or collectively programmed to control the operation of the microfluidic device and/or the detection module. For example, in some cases, the one or more computer processors may be individually or collectively programmed to load the sample into the microfluidic device, direct the sample to the at least one fluid channel for analyte extraction and separation, direct the analytes to the detector of the detection module and subsequently detect the presence or absence of the analytes using the detector.

Each part of the systems may be integrated with or separated from other parts of the systems. For example, in some cases, the detection module may be separated from the microfluidic device and the computer control system. In some cases, the detection module may be integrated with the microfluidic device, but separated from the computer control system. The microfluidic device may be integrated with the computer control system, while separated from the detection module. As an alternative, the microfluidic device may be separate from the computer control system.

The detection module of the present disclosure may comprise a single detector or a plurality of detectors. Non-limiting examples of detectors may include Flame ionization detector (FID), Aerosol-based detector (NQA), Flame photometric detector (FPD), Atomic-emission detector (AED), Nitrogen Phosphorus Detector (NPD), Evaporative light scattering detector (ELSD), Mass spectrometer (MS) (e.g., quadrupole MS, orthogonal MS etc.), UV detectors (e.g., diode array detector (DAD or PDA)), Thermal conductivity detector (TCD), Fluorescence detector, Electron capture detector (ECD), Conductivity monitor, Photoionization detector (PID), Refractive index detector (RI or RID), Radio flow detector, Chiral detector, or combinations thereof. Examples of detectors that may be used with methods and systems of the present disclosure are found in U.S. Pat. No. 8,022,361, U.S. Patent Publication No. 2014/0110661, and PCT Patent Publication No. WO 2014/093080, each of which is incorporated herein by reference in its entirety. In some cases, the detector is a mass spectrometer. In some cases, the detector is any detector other than a mass spectrometer.

In cases where a mass spectrometer is utilized, the presence or absence of the analytes or subsets thereof may be detected based on their ionization patterns in the mass spectrometer. The microfluidic device may be configured to extract the analytes from the sample, separate the extracted analytes into subsets of the analytes, and direct the subsets of the analytes through the nozzle to the detector. Electrospray ionization (ESI) is a technique used in mass spectrometry to produce ions. It is especially useful in producing ions from macromolecules (such as proteins) because it overcomes the propensity of these molecules to fragment when ionized. The ions are accelerated under vacuum in an electric filed and separated by mass analyzers according to their m/z ratios. Exemplary mass analyzers include triple-quadrupole, time-of-flight (TOF), magnetic sector, Orbitrap, ion trap, quadrupole-TOF, and Fourier transform ion cyclotron resonance (FTICR) analyzers. As individual ions reach the detector, they are counted.

In some examples, the systems of the present disclosure comprise a microfluidic device which comprises a first fluid channel, a second fluid channel in fluid communication with the first fluid channel, and at least one emitter in fluid communication with the second fluid channel. The first fluid channel may comprise a first separation medium which is adapted to extract one or more analytes from a sample obtained from a subject. The second fluid channel may comprise a second separation medium adapted to separate the one or more analytes extracted from the first fluid channel into subsets of analytes along the second fluid channel. The subsets of analytes may then be directed to the at least one emitter which is in fluid communication with the second fluid channel. The at least one emitter may comprise at least one nozzle. The at least one nozzle may be a nanotube (e.g., with a cross-section in the nanometer range) or microtube (e.g., with a cross-section in the micrometer range). The at least one nozzle may be operatively coupled to at least one detector of a detection module comprised in the systems, which detector is configured to generate signals upon exposure to the subsets of the analytes. In some cases, each subset of analytes may comprise an individual analyte among the one or more analytes extracted from the sample. The generated signals may be indicative of the subsets of analytes.

The systems may further comprise a computer control system having one or more computer processors. The one or more computer processors may be individually or collectively programmed to (1) direct the sample through the first fluid channel to extract the analytes from the sample; (2) direct the analytes extracted in the first fluid channel to the second fluid channel to separate the extracted analytes into subsets of analytes along the second fluid channel; and (3) direct the subsets of analytes from the second fluid channel through the at least one nozzle of the emitter to the detector, the detector then generating signals that are indicative of a presence or absence of each of the subsets of analytes in the sample. In some cases, the computer processors are further programmed, individually or collectively, to identify a biological state or condition of the subject based on the presence or absence of each of the subsets of analytes in the sample. The determination of the presence or absence of each of the subsets of analytes may comprise determining a concentration or an amount (absolute amount or relative amount) of each subset of the analytes.

In some cases, in addition to the first and the second fluid channels, the microfluidic device as included in the systems may further comprise one or more additional fluid channels. For example, the microfluidic device may further comprise a third fluid channel. The third fluid channel may be between and in communication with the first and the second fluid channels. The third fluid channel may or may not comprise a separation medium. In cases where a separation medium is included in the third fluid channel, it may or may not the same as the first separation medium and/or the second separation medium. In some cases, the third fluid channel comprises a barrier structure to achieve a thorough, efficient and rapid mixing of multiple fluid flows in the channel.

In some cases, the microfluidic device may comprise at least one fluid port, functioning as, e.g., fluid inlet and/or outlet. The fluid ports may be in fluid communication with at least one of the fluid channels in the microfluidic device. For example, the fluid port may be in fluid communication with the first fluid channel and configured to receive the sample and direct the sample to the first fluid channel.

In some cases, the system may comprise a plurality of fluid ports, each in fluid communication with one or more fluid channels in the microfluidic device. For example, the systems may comprise at least about 2, 3, 4, 5, 6, 7, 8, 9, 10, 11, 12, 13, 14, 15, 16, 17, 18, 19, 20 or more fluid ports. The system may further comprise at least one value and/or pump, which is operatively coupled to one or more fluid ports. The at least one value and/or pump may be configured to define flow paths in the microfluidic device. The valve may or may not be integrated with the microfluidic device. Any number of valves (or pumps) may be included in the system, for example, about 2, 3, 4, 5, 6, 7, 8, 9, 10, 11, 12, 13, 14, 15, or more. A variety of valves may be employed in the systems of the present disclosure, for example, directional control valve adapted to control and allow fluid flow into different paths from one or more sources. Non-limiting examples of valves include, but are not limited to, position valves such as two position-, three position- and proportional valve, switching valves, bonded spool valves, poppet valves, and any type of manually-, mechanically-, hydraulically- or solenoid-operated valves.

Also provided herein are methods for detecting a presence or absence of one or more analytes in a sample of a subject. The presence or absence of the one or more analytes in the sample may be indicative of or associated with a biological state or condition of the subject. The methods may comprise providing a microfluidic device having at least one fluid channel in fluid communication with at least one emitter. The fluid channel may comprise a separation medium which is adapted to separate the one or more analytes into subsets of the analytes or individual ones. The at least one emitter may comprise at least one nozzle, which may be operatively coupled to at least one detector. The detector(s) may or may not be integrated with the microfluidic device and may be configured to generate signals upon exposure to the analytes or subsets thereof. In some cases, the at least one nozzle may extend from a base tube which is in fluid communication with the at least one fluid channel. Cross-sectional dimension of the base tube may be larger than, smaller than or the same as that of the at least one nozzle. The at least one nozzle and the base tube may be monolithic. In some cases, the at least one emitter may include a plurality of emitters, such as at least 2, 3, 4, 5, 6, 7, 8, 9, 10, 20, 30, 40, or 50 or more emitters. The at least one nozzle may include a plurality of nozzles, such as at least 2, 3, 4, 5, 6, 7, 8, 9, 10, 20, 30, 40, 50, 100 or more nozzles per emitter.

In some case, the microfluidic device may have a plurality of fluid channels in fluid communication with one another. For example, the microfluidic device may comprise a first fluid and a second fluid channel in fluid communication with the first fluid channel. The first fluid channel and the second fluid channel may be configured to perform the same or different functions or procedures (e.g., sample processing, treatment, purification, concentration, and/or separation) on the sample. In some cases, the first fluid channel is configured to receive a raw sample obtained from the subject and perform sample processing (e.g., SPE) on the microfluidic device by extracting or isolating the one or more analytes from the raw sample. A separation medium may be comprised in the first fluid channel and may be adapted to extract or isolate the analytes from the sample. The second fluid channel may also comprise a separation medium, which separation medium may be adapted to separate the one or more analytes extracted from the first fluid channel into subsets of analytes along the channel.

The second fluid channel may further comprise an enrichment channel and a separation channel downstream of the enrichment channel. The enrichment channel may be in fluid communication with the first fluid channel and configured to purify and/or concentrate the one or more analytes extracted from the first fluid channel as they move along the enrichment channel. The separation channel may be adapted to receive the one or more analytes purified and/or concentrated in the enrichment channel and separate them into subsets of the analytes or individual ones along the separation channel. In some cases, the microfluidic device may further comprise a third microfluidic channel for, e.g., facilitating mixing of the one or more analytes from the first fluid channel with a solvent before they reach the second fluid channel. The third fluid channel may be between and in fluid communication with both the first fluid channel and the second fluid channel. The third fluid channel may include a barrier structure, whose cross-section (or height) may be less than a height of the third fluid channel. The barrier structure may comprise periodic structures. The structures may be symmetrical or asymmetrical. In some cases, the barrier structure comprises one or more sets of periodic structures, each set comprising the same or a different type of shaped structures. In some cases, the barrier structure comprises staggered herringbone grooves or chevron-shaped grooves. The height of the barrier structure may vary, depending upon various factors, for example, dimensions of the third fluid channel. In some cases, the height of the barrier structure may be greater than or equal to about 0.01 micron ($\mu m$), 0.05 $\mu m$, 0.1 $\mu m$, 0.2 $\mu m$, 0.3 $\mu m$, 0.4 $\mu m$, 0.5 $\mu m$, 0.6 $\mu m$, 0.7 $\mu m$, 0.8 $\mu m$, 0.9 $\mu m$, 1 $\mu m$, 5 $\mu m$, 10 $\mu m$, 15 $\mu m$, 20 $\mu m$, 25 $\mu m$, 30 $\mu m$, 35 $\mu m$, 40 $\mu m$, 45 $\mu m$, 50 $\mu m$, 55 $\mu m$, 60 $\mu m$, 65 $\mu m$, 70 $\mu m$, 75 $\mu m$, 80 $\mu m$, 85 $\mu m$, 90 $\mu m$, 95 $\mu m$, 100 $\mu m$, 110 $\mu m$, 120 $\mu m$, 130 $\mu m$, 140 $\mu m$, 150 $\mu m$, 160 $\mu m$, 170 $\mu m$, 180 $\mu m$, 190 $\mu m$, 200 $\mu m$ or more. In some cases, the height of barrier structure may be less than or equal to about 1,000 $\mu m$, 800 $\mu m$, 600 $\mu m$, 400 $\mu m$, 200 $\mu m$, 100 $\mu m$, 90 $\mu m$, 85 $\mu m$, 80 $\mu m$, 75 $\mu m$, 70 $\mu m$, 65 $\mu m$, 60 $\mu m$, 55 $\mu m$, 50 $\mu m$, 40 $\mu m$, 30 $\mu m$, 20 $\mu m$, 10 $\mu m$, 5 $\mu m$, 1 $\mu m$ or less. In some cases, the height of barrier stricture may be between any of the two values described herein. In cases where the barrier structure comprises one or more sets of periodic structures, the height of the structure within each set may be the same or different from one another.

The separation media comprised in the first and the second fluid channels may or may not be the same. The separation media may be polar or non-polar. The separation media may comprise solid materials. In some cases, the separation media comprise beads and/or porous structures, such as, silica with or without surface modifications. In some cases, the porous structures are monolithic structures.

The methods of the present disclosure may further comprise the step of directing the sample to the at least one fluid channel of the microfluidic device under conditions that permit the one or more analytes to be separated into the subsets of the analytes or individual ones along the fluid channel. The sample may be directed to the fluid channel without any prior processing or treatment procedures and the fluid channel may be adapted to perform sample processing/treatment on the microfluidic device. Volume of the sample may vary, depending upon, for example, availability of the sample source and specific applications. In some cases, the sample volume is less than or equal to 200 microliters ($\mu l$), 150 $\mu l$, 125 $\mu l$, 100 $\mu l$, 90 $\mu l$, 80 $\mu l$, 70 $\mu l$, 60 $\mu l$, 55 $\mu l$, 50 $\mu l$, 45 $\mu l$, 40 $\mu l$, 35 $\mu l$, 30 $\mu l$, 25 $\mu l$, 20 $\mu l$, 15 $\mu l$, 10 $\mu l$, 9 $\mu l$, 8 $\mu l$, 7 $\mu l$, 6 $\mu l$, 5 $\mu l$, 4 $\mu l$, 3 $\mu l$, 2 $\mu l$, 1 $\mu l$, 0.8 $\mu l$, 0.6 $\mu l$, 0.4 $\mu l$, 0.2 $\mu l$, 0.1 $\mu l$, 0.05 $\mu l$, 0.01 $\mu l$, or less.

Next, the subsets of the analytes (or individual ones) separated from the fluid channel may be directed from the fluid channel to the at least one nozzle, followed by the step of directing the subsets of the analytes from the at least one nozzle to the detector which is operatively coupled to the nozzle. The presence or absence of the subsets of the analytes may then be detected based on signals generated upon exposure of the detector to the subsets of analytes. As provided herein, the steps from sample loading to signal detection may be performed in a short time period. For example, such time period may be less than or equal to about 48 hours, 36 hours, 24 hours, 12 hours, 10 hours, 8 hours, 6 hours, 5 hours, 4 hours, 3 hours, 2 hours, 1 hour, 50 minute (min), 45 min, 40 min, 35 min, 30 min, 25 min, 20 min, 15 min, 10 min, 9 min, 8 min, 7 min, 6 min, 5 min, 4 min, 3 min, 2 min, 1 min, or less.

In some cases, the methods further comprise generating an electronic report that is indicative of the presence or absence of the one or more analytes in the sample. The electronic report may be provided for display on a user interface (UI) of an electronic device of a user, such as a graphical user interface (GUI). The user may be the subject. The user may be a healthcare provider of the subject. Based on the presence or absence of the one or more analytes in the sample, a biological state or condition of the subject may be identified. In some cases, the biological state or condition is identified based on the presence or absence of the subsets of the analytes. Each of the subsets may include an individual analyte among the one or more analytes included in the sample. In some cases, the methods may further comprise detecting the presence or absence of the subsets of substances at multiple time points to monitor a progression of the biological state or condition in a subject. The methods may also comprise providing a therapeutic intervention upon identifying the biological state or condition of the subject.

As provided herein, any substance that is detectable or measurable may be an analyte. For example, the analytes may be any type of organic or inorganic molecules, compounds and/or compositions, such as biomolecules. In some cases, the analytes comprise chemicals such as environmental chemicals, nutritional indicators, radiologic threat agents, metals, lipids, glycans, saccharides (e.g., monosaccharides, oligosaccharides and polysaccharides), proteins, peptides, antibodies, enzymes, aptamers, nucleic acids, antigens, cells, tissues, biomarkers, or disease-causing agents such as viruses, bacteria, fungi, protozoa, and worms. In some cases, the protein may be derived from cell or tissue lysate, body fluid, or other sample source, such as in the case of reverse phase protein array analysis. In some cases, the analytes comprise perfluorinated compounds (PFCs) and/or any types of environmental toxins.

Non-limiting examples of analytes include, but are not limited to, Acephate, Acetochlor, Acrylamide, Alachlor, Aldrin/Dieldrin, Antimony, Arsenic, Atrazine, Barium, Benzene, biomarkers, Bromodichloromethane, Benzophenone-3, Benzylbutyl Phthalate, Beryllium, Bisphenol A, Carbofuran, Cadmium, Cesium, Chlordane/Heptachlor, Chlorobenzenes, Chlorpyrifos/Chlorpyrifos-methyl, Cobalt, Cotinine, Coumaphos, Cyfluthrin, Cyfluthrin/Cypermethrin/Permethrin,Cyhalothrin/Cypermethrin/Deltamethrin/Fenpropathrin/Permethrin/Tralomethrin, Deltamethrin, Di-2-ethylhexyl Phthalate, Diazinon, 1,2-Dibromo-3-Chloropropane (DBCP), 2,4-Dichlorophenol, 2,5-Dichlorophenol, Dichlorodiphenyltrichloroethane (DDT), 2,4-Dichlorophenoxyacetic Acid, Dibromochloromethane (Chlorodibromomethane), Dicyclohexyl Phthalate, Diethyl Phthalate, Di-isodecyl phthalate, Di-isononyl Phthalate, Dimethoate/Omethoate, 2,5-Dimethylfuran, Dimethyl Phthalate, Di-n-butyl Phthalate/Di-isobutyl Phthalate, Di-n-octyl Phthalate, Dioxin-Like Chemicals, Diethylphosphate (DEP), Dimethylphosphate (DMP), Diethylthiophosphate (DETP), Dimethylthiophosphate (DMTP), Diethyldithiophosphate (DEDTP), Dimethyldithiophosphate (DMDTP), Polychlorinated Dibenzo-p-dioxins, Polychlorinated Dibenzofurans, and Coplanar and Mono-ortho-substituted Polychlorinated Biphenyls, Disinfection By-Products (Trihalomethanes), Environmental Phenols (e.g., trans-3-(2,2-Dichlorovinyl)-2,2-dimethylcyclopropane carboxylic acid, cis-3-(2,2-Dibromovinyl)-2,2-dimethylcyclopropane carboxylic acid, 4-Fluoro-3-phenoxybenzoic acid, 3-Phenoxybenzoic acid), Endrin, Ethylbenzene, Ethylene thiourea/Propylene thiourea, Fluorene, Fungicides and Metabolites, Halogenated Solvents, Hexachlorobenzene, Herbicides and Metabolites such as 2,4-Dichlorophenoxyacetic acid, and 2,4,5-Trichlorophenoxyacetic acid, Hexachlorocyclohexane, Hexachloroethane, Lead, Malathion, Mercury, Metals and Metalloids including Antimony, Inorganic Arsenic-related Species, Arsenic (V) acid, Arsenobetaine, Arsenocholine, Arsenous (III) acid, Dimethylarsinic acid, Monomethylarsonic acid, Trimethylarsine oxide, Beryllium, Copper, Manganese, Mercury (total; inorganic; ethyl and methyl species), Molybdenum, Platinum, Selenium, Strontium, Sulfonylurea Herbicides (e.g., Bensulfuron-methyl, Chlorsulfuron, Ethametsulfuron-methyl, Foramsulfuron, Halosulfuron, Mesosulfuron-methyl, Metsulfuron-methyl, Nicosulfuron, Oxasulfuron, Primisulfuron-methyl, Prosulfuron, Rimsulfuron, Sulfometuron-methyl, Sulfosulfuron, Thifensulfuron-methyl, Triasulfuron and Triflusulfuron-methyl), Thallium, Tin, Tungsten, Uranium, Zinc, Benzophenone-3, Bisphenol A, 4-tert-Octylphenol, Triclosan Methamidophos, Methyl Parathion/Ethyl Parathion, Methyl tert-Butyl Ether (MTBE), Metolachlor, Mirex, Molybdenum, Naphthalene, Nitrobenzene, NNAL (4-(methylnitrosamino)-1-(3-pyridyl)-1-butanol), N,N-Diethyl-meta-toluamide (DEET), Non-Dioxin-Like Polychlorinated Biphenyls, 4-tert-Octylphenol, Organophosphorus Insecticides: Dialkyl Phosphate Metabolites, ortho-Phenylphenol, Other Halogenated Solvents, Parabens including Butyl paraben, Ethyl paraben, Methyl paraben, n-Propyl paraben, ortho-Phenylphenol, Ethylene thiourea, Pentachlorophenol, and Propylene thiourea, Pentachlorophenol, Perchlorate, Perfluorochemicals, Phenanthrene, Phytoestrogens, Pirimiphos-methyl, Platinum, Polybrominated Diphenyl Ethers and 2,2',4,4',5,5'-Hexabromobiphenyl (BB-153), Propoxur, Pyrene, Styrene, Sulfonylurea Herbicides, Thallium, Toluene, Trichlorophenols, Tribromomethane (Bromoform), Trichloromethane (Chloroform) 2,4,5-Trichlorophenoxyacetic Acid, Triclosan, Tungsten, Uranium, Xylenes. Perfluorinated Compounds Surfactants (e.g., Perfluorobutane sulfonic acid (PFBuS), Perfluorodecanoic acid (PFDeA), Perfluorododecanoic acid (PFDoA), Perfluoroheptanoic acid (PFHpA), Perfluorohexane sulfonic acid (PFHxS), Perfluorononanoic acid (PFNA), Perfluorooctanoic acid (PFOA), Perfluorooctane sulfonic acid (PFOS), Perfluorooctane sulfonamide (PFOSA), 2-(N-Ethyl-perfluorooctane sulfonamido) acetic acid (Et-PFOSA-AcOH), 2-(N-Methyl-perfluorooctane sulfonamido) acetic acid (Me-PFOSA-AcOH), Perfluoroundecanoic acid (PFUA), Aldrin, Dieldrin, Endrin, Heptachlor epoxide, o,p'-Dichlorodiphenyltrichloroethane (DDT), 2,4,5-Trichlorophenol, and 2,4,6-Trichlorophenol), Other Pesticides and Metabolites (e.g., 2,4-Dichlorophenol, 2,5-Dichlorophenol), Organophosphorus Insecticides: Specific Metabolites (e.g., Acephate, Dimethoate, Methamidophos, Omethoate, Malathion dicarboxylic acid, 2-Isopropyl-4-methyl-6-hydroxypyrimidine, para-Nitrophenol, and 3,5,6-Trichloro-2-pyridinol), or combination thereof.

With the methods and systems of the present disclosure, the analytes (including subsets of analytes and individual analytes) can be detected at a high sensitivity (or accuracy), which can be determined by the average percentage of the expected amount for the analytes at a certain concentration. In some cases, the analytes are detected at a sensitivity (or accuracy) of at least about 60%, 65%, 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, or 99%. In some cases, the sensitivity falls between any of the two values described herein, for example, about 88.22%.

In some cases, the analytes are detected at a high specificity (or precision), which is defined as a ratio of desired signals from the analytes to the whole signals obtained. In some cases, the analytes are detected at a specificity (or precision) of at least about 60%, 65%, 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, or 99%. In some cases, the specificity (or precision) falls between any of the two values described herein, for example, about 90.5%.

In some cases, the analytes are detected at a low value of limit of detection (LOD). The "LOD" (or detection limit), as used herein, is determined using the lowest concentration in a calibration curve, with a certain level of signal-to-noise (S/N) ratio. With a fixed S/N ratio, for example, at least about 1, 2, 3, 4, 5, 6, 7, 8, 9, 10, or higher, the detection limit of the analytes may be less than or equal to about 100 nanogram/milliliter (ng/ml), 80 ng/ml, 60 ng/ml, 40 ng/ml, 20 ng/ml, 10 ng/ml, 9 ng/ml, 8 ng/ml, 7 ng/ml, 6 ng/ml, 5 ng/ml, 4 ng/ml, 3 ng/ml, 2 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, 0.1 ng/ml, 0.09 ng/ml, 0.08 ng/ml, 0.07 ng/ml, 0.06 ng/ml, 0.05 ng/ml, 0.04 ng/ml, 0.03 ng/ml, 0.02 ng/ml, 0.01 ng/ml, or less. In some cases, the limit of detection may be determined by the absolute amount of the analytes, at a per-defined level of S/N ratio. For example, the LOD of the analytes may be less than or equal to about 100 picograms (pg), 80 pg, 60 pg, 40 pg, 20 pg, 10 pg, 5 pg, 1 pg, 800 femtograms (fg), 600 fg, 500 fg, 400 fg, 350 fg, 300 fg, 250 fg, 200 fg, 150 fg, 100 fg, 95 fg, 90 fg, 85 fg, 80 fg, 75 fg, 70 fg, 65 fg, 60 fg, 55 fg, 50 fg, 45 fg, 40 fg, 35 fg, 30 fg, 25 fg, 20 fg, 15 fg, 10 fg, 9 fg, 8 fg, 7 fg, 6 fg, 5 fg, 4 fg, 3 fg, 2 fg, 1 fg, or less.

Microfluidic Devices

A microfluidic device of the present disclosure may include one or more fluid channels in fluid communication with one another. The one or more fluid channels may be etched or molded into a material (e.g., glass, silicon or polymer etc.). The one or more fluid channel in the microfluidic device may individually or collectively perform the same or different functions (e.g., sample loading, processing, transporting, purification, concentration, enrichment, and separation etc.). The microfluidic device may be a chip (e.g., a single-plex chip, a multi-plex chip) or a part of the chip. A chip may be assembled from a plurality of multiple multi-layer microfluidic devices using manifolds and clamps. The chip may have a feature of disposability or multi-uses. The microfluidic device may be disposable or reusable. For example, in some cases, the microfluidic device may be single use for a single sample or a plurality of samples. In some cases, the microfluidic device may be multi-use for a single sample or a plurality of samples.

The number of fluid channels and emitters included in the device may vary, depending upon, applications of the device. For example, a plurality of fluid channels may be preferred in cases where multiple procedures are to be performed on a sample and/or a plurality of samples need to be analyzed in parallel. In some cases, a large number of fluid channels may be included in the device. In some cases, a small number of fluid channels may be included in the device. In some cases, the microfluidic device may comprise greater than or equal to about 1, 2, 3, 4, 5, 6, 7, 8, 9, 10, 15, 20, 25, 30, 35, 40, 50, 60, 70, 80, 90, 100, or more fluid channels. In some cases, the microfluidic device may comprise less than about 300, 250, 200, 150, 100, 90, 80, 70, 60, 50, 40, 30, 20, 15, 14, 13, 12, 11, 10, 9, 8, 7, 6, 5, 4, 3, or 2 fluid channels. In some cases, the number of fluid channels included in the device may be between any of the two values described herein.

As provided herein, at least one fluid channel may be used for performing various procedures on the sample obtained from a subject. For example, the fluid channel may be configured to perform sample preparation, processing, treatment, purification, concentration and/or separation on the sample in the microfluidic device. The sample may be loaded into the microfluidic device with or without prior sample preparation or processing. Each procedure may comprise one or more steps. In cases where multiple steps are included in a procedure, the steps may or may not occur at the same location (e.g., within the same fluid channel) in the microfluidic device. In some cases, it may be preferred to have some or all of the steps performed in the microfluidic device.

In some cases, the microfluidic device may include a layered structure that monolithically integrates several functional modules (e.g., fluid channels) on a single device. Non-limiting examples of functional fluid channels may include sample loading channel (or sample input, sample inlet), sample preparation channel, sample processing/treatment channel, purification channel, mixing channel, concentration channel, extraction channel (or extraction segment), trap channel (or trap column), enrichment channel, separation channel, make-up channel, sample exit channel (or sample outlet), or combinations thereof. As discussed above and elsewhere herein, a fluid channel may be configured to perform sample preparation and/or processing procedures on a sample when the sample is received without prior processing or treatment. The fluid channel may be configured to perform a variety of sample preparation and/or processing procedures on the sample, including, e.g., filtration, liquid-liquid extraction, solid supported liquid extraction (SLE), and solid-phase extraction (SPE) including reversed phase SPE, cation exchange SPE, anion exchange SPE, mixed mode SPE, and specialty SPE.

The fluid channel may be of different shapes, e.g., cube, cuboid, cone, cylinder, prism, pyramid, or any regular or irregular shapes. In cases where more than one fluid channels are comprised in the device, each of the fluid channels may be of the same or a different shape. In some cases, a certain percentage of the fluid channels may have the same or a different shape, for example, 99% of the fluid channels may have the same shape.

The length of the fluid channel may vary, depending upon, for example, quantity, acidity, basicity, charge, size, architecture, hydrophilicity, hydrophobicity, and affinity of the analyte. In some cases, a longer fluid channel may be preferred. In some cases, a shorter fluid channel may be used. In some cases, the length of the fluid channel may be less than or equal to about 1,000 millimeters (mm), 900 mm, 800 mm, 700 mm, 600 mm, 500 mm, 400 mm, 300 mm, 200 mm, 150 mm, 140 mm, 130 mm, 120 mm, 110 mm, 100 mm, 95 mm, 90 mm, 85 mm, 80 mm, 75 mm, 70 mm, 65 mm, 60 mm, 55 mm, 50 mm, 45 mm, 40 mm, 35 mm, 30 mm, 25 mm, 20 mm, 15 mm, 10 mm, 5 mm, 1 mm, 0.5 mm, 0.1 mm or shorter. In some cases, the length of the fluid channel may be at least about 0.001 mm, 0.005 mm, 0.01 mm, 0.05 mm, 0.1 mm, 0.5 mm, 1 mm, 5 mm, 7.5 mm, 10 mm, 20 mm, 30 mm, 40 mm, 50 mm, 60 mm, 70 mm, 80 mm, 90 mm, 100 mm, 120 mm, 140 mm, 160 mm, 180 mm, 200 mm, 400 mm, 600 mm, 800 mm, or longer. In some cases, the length of the channel may be between any of two values described herein. In cases where a plurality of fluid channels is included in the microfluidic device, each channel may or may not have the same length. In some cases, a certain percentage of the fluid channels have the same length, for example, about 1%, 5%, 10%, 15%, 20%, 25%, 30%, 35%, 40%, 45%, 50%, 55%, 60%, 65%, 70%, 75%, 80%, 85%, 90%, 95%, or 99% of the fluid channels have the same length. In some cases, the percentage of the fluid channels which have the same length falls between any of the two values described herein.

In some cases, the fluid channel may have a cross-section that is of a certain shape, for example, square, triangular, rectangular, circular, polygonal, or any types of regular or irregular shapes. Dimensions (i.e., cross-sectional dimension) of the fluid channel may vary. For example, the fluid channel may have at least one dimension (e.g, width, depth, diameter) less than or equal to about 5,000 microns (µm), 4,000 µm, 3,000 µm, 2,000 µm, 1,000 µm, 750 µm, 500 µm, 450 µm, 400 µm, 350 µm, 300 µm, 250 µm, 200 µm, 190 µm, 180 µm, 170 µm, 160 µm, 150 µm, 140 µm, 130 µm, 120 µm, 110 µm, 100 µm, 90 µm, 80 µm, 70 µm, 50 µm, 30 µm, 10 µm, 5 µm, 1 µm, or less. In some cases, the fluid channel may have at least one dimension greater than or equal to about 1 µm, 5 µm, 10 µm, 25 µm, 50 µm, 75 µm, 80 µm, 90 µm, 100 µm, 110 µm, 120 µm, 130 µm, 140 µm, 145 µm, 150 µm, 160 µm, 170 µm, 180 µm, 190 µm, 200 µm, 250 µm, 300 µm, 350 µm, 400 µm, 450 µm, 500 µm, 750 µm, 1,000 µm, or more. In some cases, the fluid channel may have at least one dimension in between any of the two values described herein.

As provided herein, in cases where the microfluidic device comprises more than one fluid channels. The dimensions of each fluid channel may or may not vary. In some cases, all of the fluid channels may have the same dimensions. In some cases, each fluid channel may be of different dimension. In some cases, a certain percentage of the fluid channels may be of the same dimensions. In some cases, it may be desired that a certain percentage of the fluid channels are of the same dimensions, e.g., about 5%, 10%, 15%, 20%, 25%, 30%, 35%, 40%, 50%, 60%, 70%, 80%, 90%, or 100% of the fluid channels.

Flow rates in the fluid channels may vary, dependent upon, for example, channel dimensions. For example, a fluid channel with smaller cross-sectional dimensions may require a lower flow rate. In cases where more than one fluid flows (or streams) are directed to and mixed within the same fluid channel, flow rates of different fluid flows may or may not vary. For each fluid flow, the flow rate may or may not change with time. For example, in some cases, a fluid flow passes along the one or more fluid channels at a constant flow rate. In some cases, the flow rate of the fluid flow continuously changes with the time. In some cases, the flow rate of the fluid flow changes with time initially and then is held at a constant level for a certain period of time.

Various methods or techniques may be used for sample separation. Non-limiting examples of methods or techniques may include Column Chromatography, Paper Chromatography, Thin Layer Chromatography, Gas Chromatography, Liquid Chromatography, Supercritical Fluid Chromatography, Ion Exchange Chromatography, Size-exclusion Chromatography, Expanded Bed Adsorption (EBA) Chromatographic Separation, Two-dimensional Chromatography, Simulated moving-bed Chromatography, Pyrolysis Gas Chromatography, Fast Protein Liquid Chromatography, Countercurrent Chromatography, Chiral Chromatography, Capillary Electrophoresis, Capillary Gel Electrophoresis, Capillary Zone Electrophoresis, Capillary Isoelectric Focusing, Capillary Electrochromatography, or combinations thereof. As provided herein, at least one fluid channel may be adapted to separate substances of interest included in a sample, based on one or more of the abovementioned separation techniques. For example, in some cases, the microfluidic device may comprise at least one fluid channel (or LC-column) to perform Liquid Chromatography on the sample.

As provided herein, the separation media may comprise porous monoliths directly fabricated inside the column, which may be porous structures characterized by mesopores and macropores. As an alternative or in addition to, the separation media may comprise a plurality of particles, solid or semi-solid (e.g., silica particles, polymer particles, sorbents, or beads) with the same or varying sizes, porosity, and functional groups. In some cases, all of the particles have the same size. In some cases, each of the particles may have a different size. In some cases, a certain percentage of the particles may have the same size. Particle size (or dimensions) may vary, depending upon, for example, column length, chemical and/or physical properties of the sample and/or analytes, resolution, detection limits, type of eluants used, desired specificity, sensitivity, accuracy and/or precision etc.

In some cases, the separation media comprise beads, each having the same or a different cross-sectional dimension. The cross-sectional dimension of the beads may vary, for example, it may be greater than or equal to about 0.1 nanometer (nm), 0.5 nm, 1 nm, 5 nm, 10 nm, 15 nm, 20 nm, 40 nm, 60 nm, 80 nm, 100 nm, 200 nm, 300 nm, 400 nm, 500 nm, 600 nm, 700 nm, 800 nm, 900 nm, 1 micrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 17 µm, 19 µm, 20 µm, 30 µm, 40 µm, 50 µm, 60 µm, 70 µm, 80 µm, 90 µm, 100 µm, 200 µm, or more. In some cases, the beads have a cross-sectional dimension less than or equal to about 500 µm, 400 µm, 300 µm, 200 µm, 150 µm, 100 µm, 90 µm, 80 µm, 70 µm, 60 µm, 50 µm, 40 µm, 30 µm, 25 µm, 20 µm, 18 µm, 16 µm, 14 µm, 12 µm, 10 µm, 8 µm, 7 µm, 6 µm, 5 µm, 4 µm, 3 µm, 2 µm, 1 µm, 800 nm, 600 nm, 400 nm, 200 nm, 100 nm, 75 nm, 50 nm, 25 nm, 10 nm, 5 nm, 1 nm or less. In some cases, the cross-sectional dimension of the beads falls between any of the two values described herein, for example, the beads may have a cross-sectional dimension from about 20 nanometers or less to about 1 micrometer. In some cases, the beads have a narrow size distribution. In some cases, the beads have a broad size distribution. In some cases, the separation media may comprise one or more functional groups, such as alky chains. The alkyl chains may range from C1 (i.e., methyl), to C30, for example, C4, C8, or C18.

The beads may be porous and each of the beads may have a plurality of pores. The plurality of pores may have a narrow or a broad size distribution. The pore size may vary, from very small to very large, depending upon, e.g., the type of beads utilized. For example, in cases where C18 beads are used, each pore has a pore size from about 1 nm to about 30 nm or more. In some cases where C4 beads are used, each of the plurality of pores has a pore size from about 1 nm to about 10 nm or more. In some cases, the pore size is greater than or equal to about 0.01 nm, 0.05 nm, 0.075 nm, 0.1 nm, 0.5 nm, 1 nm, 2 nm, 3 nm, 4 nm, 5 nm, 6 nm, 7 nm, 8 nm, 9 nm, 10 nm, 11 nm, 12 nm, 13 nm, 14 nm , 15 nm, 16 nm, 17 nm, 18 nm, 19 nm, 20 nm, 22 nm, 24 nm, 26 nm, 28 nm, 30 nm, 35 nm, 40 nm, 45 nm, 50 nm, 55 nm, 60 nm, 80 nm, 100 nm, 200 nm, or more. In some cases, the pore size is smaller than or equal to about 500 nm, 400 nm, 300 nm, 200 nm, 100 nm, 80 nm, 60 nm, 40 nm, 20 nm, 10 nm, 8 nm, 6 nm, 4 nm, 2 nm, 1 nm, or less. In some cases, the pore size is between any of the two values described herein.

Various solvents may be used in the present disclosure, including, e.g., organic, inorganic, or mixed solvent. Non-limiting examples of solvents may include water, methanol, propanol, acetonitrile, dioxane, ethyl acetate, acetone, diethyl ether, tetrahydrofuran, methylene chloride, chloroform, carbon tetrachloride, isooctane, hexane, or combinations thereof. In some cases, solvent gradient may be required when performing certain procedures, such as sample separation. Gradients may be linear or non-linear. Gradients may have multiple segments.

As described above and elsewhere herein, microfluidic devices of the present disclosure may include one or more emitters. The number of emitters comprised in each microfluidic device may vary. In some cases, a large number of emitters may be comprised in the microfluidic device. In some cases, a small number of emitters may be comprised in the device. In some cases, each microfluidic device may comprise greater than or equal to about 1, 2, 3, 4, 5, 6, 7, 8, 9, 10, 15, 20, 25, 30, 35, 40, 45, 50, 60, 70, 80, 90, 100, or more emitters. In some cases, each microfluidic device may comprise less than about 500, 400, 300, 200, 100, 90, 80, 70, 60, 50, 40, 30, 20, 15, 14, 13, 12, 11, 10, 9, 8, 7, 6, 5, 4, 3, 2, or 1 emitter. In some cases, the number of emitters comprised in each microfluidic device may be between any of the two values described herein.

The emitter may further comprise at least one base tube (or base channel) and at least one nozzle, wherein the base tube is in fluidic communication with both the nozzle and at least one fluid channel. In some cases, the base tube has the same cross-sectional dimension as the nozzle. In some cases, the base tube has a larger cross-sectional dimension than the nozzle. In some cases, the base tube has a smaller cross-sectional dimension than the nozzle. In cases where multiple emitters are included, each emitter may comprise equal numbers of base tubes and nozzles, and each base tube is in fluid communication with each of the nozzles. In some cases, each emitter comprises a different number of base tubes and nozzles, and more than one of the base tubes (or nozzles) may be in fluid communication with each of the nozzles (or base tubes).

In some cases, each emitter comprises at least about 1, 2, 3, 4, 5, 6, 7, 8, 9, 10, 15, 20, 25, 30, 35, 40, 45, 50, 60, 70, 80, 90, 100, or more base tubes. In some cases, each emitter may comprises less than or equal to about 300, 250, 200, 150, 100, 90, 80, 70, 60, 50, 40, 30, 20, 15, 14, 13, 12, 11, 10, 9, 8, 7, 6, 5, 4, 3, 2, or 1 base tubes. In some cases, the number of base tubes comprised in each emitter falls between any of the two values described herein, for example, 12, or 14.

In some cases, the base tube and the nozzle are integrated with each other, for example, the walls of the nozzle and the base tube may form a monolithic whole. The base tube may be separated from the nozzle. In some cases, the nozzle may extend out from the base tube and the protruding length may vary. In cases where multiple nozzles are comprised in the emitter, each of the nozzles may have the same or a different protruding length. In some cases, a certain percentage of the nozzles may have the same or a different protruding length. In some cases, at least about 1%, 5%, 10%, 15%, 20%, 30%, 40%, 50%, 60%, 70%, 75%, 80%, 85%, 90%, 91%, 92%, 93%, 94%, 95%, 96%, 97%, 98%, 99%, or 100% of the nozzles have the same or a different protruding length. In some cases, less than or equal to about 100%, 90%, 80%, 70%, 60%, 50%, 40%, 30%, 20%, 10%, 5%, or 1% of the nozzles have the same or a different protruding length.

The cross-sectional dimension of the nozzle may vary, for example, it may be greater than or equal to about 0.01 μm, 0.05 μm, 0.1 μm, 0.5 μm, 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 17 μm, 19 μm, 20 μm, 30 μm, 40 μm, 50 μm, 60 μm, 70 μm, 80 μm, 90 μm, 100 μm, 200 μm, or more. In some cases, the nozzle has a cross-sectional dimension that is less than or equal to about 500 μm, 400 μm, 300 μm, 200 μm, 150 μm, 100 μm, 90 μm, 80 μm, 70 μm, 60 μm, 50 μm, 40 μm, 30 μm, 25 μm, 20 μm, 18 μm, 16 μm, 14 μm, 12 μm, 10 μm, 8 μm, 7 μm, 6 μm, 5 μm, 4 μm, 3 μm, 2 μm, 1 μm, or less. In some cases, the cross-sectional dimension of the nozzle falls between any of the two values described herein, for example, the nozzle may have a cross-sectional dimension from about 1 μm to about 50 μm.

The spacing between the two adjacent nozzles of the multiple nozzles may vary. For example, in some cases, the spacing between the adjacent nozzles for a linear array of multiple nozzles is the same. In some cases, multiple rows of a linear array of multiple nozzles can be stacked together vertically and either symmetrically or asymmetrically into a 3D structure. In some cases, the spacing between the adjacent nozzles is different. In some cases, the spacing may be greater than or equal to about 0.1 μm, 0.5 μm, 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 17 μm, 19 μm, 20 μm, 30 μm, 40 μm, 50 μm, or more. In some cases, the spacing may be less than or equal to about 100 μm, 90 μm, 80 μm, 70 μm, 60 μm, 50 μm, 40 μm, 30 μm, 20 μm, 18 μm, 16 μm, 14 μm, 12 μm, 10 μm, 8 μm, 6 μm, 4 μm, 2 μm, 1 μm, or less. In some cases, the spacing falls between any of the two values described above, for example, from about 1 μm to about 50 μm.

Also provided in the present disclosure is that the nozzle may be sharpened. In some cases, all of the nozzles comprised in the device may be sharpened. In some cases, a certain percentage of the nozzles is sharpened, for example, about 1%, 5%, 10%, 20%, 30%, 40%, 50%, 60%, 70%, 80%, 90%, 95%, 99%, or 100% of the nozzles are sharpened. In cases where the nozzle comprises more than one side, sharpening may occur on any side of the nozzle, for example, the nozzle may be one-sided sharpened, two-sided sharpened, three-sided sharpened, four-sided sharpened, or multiple-sided sharpened. In some cases, it may be preferred that none of the sides of the nozzle is sharpened, i.e., a flat-end nozzle. In some cases, the degrees of sharpening angles vary on any side of a nozzle or on any of the nozzles within a plurality of nozzles.

Flow rate at the emitter or the nozzle may vary. In some cases, the flow rate is less than or equal to about 2,000 nl/min, 1,500 nl/min, 1,000 nl/min, 900 nl/min, 800 nl/min, 700 nl/min, 600 nl/min, 500 nl/min, 400 nl/min, 300 nl/min, 200 nl/min, 100 nl/min, 90 nl/min, 80 nl/min, 70 nl/min, 60 nl/min, 50 nl/min, 40 nl/min, 30 nl/min, 20 nl/min, 10 nl/min, 5 nl/min, 4 nl/min, 3 nl/min, 2 nl/min, 1 nl/min, 0.8 nl/min, 0.6 nl/min, 0.4 nl/min, 0.2 nl/min, 0.1 nl/min, 0.05 nl/min, 0.01 nl/min, 0.005 nl/min, 0.001 nl/min or less. In some cases, the flow rate for some fake nozzles is zero. In some cases, the flow rate is greater than or equal to about 0 nl/min, 0.1 nl/min, 0.5 nl/min, 0.75 nl/min, 1 nl/min, 1.5 nl/min, 2 nl/min, 3 nl/min, 4 nl/min, 5 nl/min, 6 nl/min, 8 nl/min, 10 nl/min, 20 nl/min, 30 nl/min, 40 nl/min, 50 nl/min, 60 nl/min, 70 nl/min, 80 nl/min, 90 nl/min, 100 nl/min, 200 nl/min, 300 nl/min, 400 nl/min, 500 nl/min, 600 nl/min, 800 nl/min, 1,000 nl/min, 2,000 nl/min, 3,000 nl/min, 4,000 nl/min, 5,000 nl/min or more. In some cases, the flow rate falls between any of the two values described herein, for example, about 65 nl/min.

The design, fabrication, structure, and applications of microfluidic device may be as described in, for example, U.S. Pat. No. 8,022,361, U.S. Patent Publication No. 2014/0110661, PCT Patent Publication No. WO 2014/093080, and PCT Patent Publication No. WO 2015/112429, each of which is incorporated herein by reference in its entirety.

Various methods or approaches may be utilized to fabricate the microfluidic device provided herein, such as etching, machining, cutting, molding, casting or embossing. As described elsewhere herein, it may be preferred to have a microfluidic device that may monolithically integrate several functional modules on a single chip. For example, a microfluidic device has at least one fluid channel in fluidic communication with at least one emitter, wherein the emitter further comprises at least a base tube and a plurality of nozzles seamlessly connected to the base tube.

The microfluidic device may be manufactured by using different types of materials. Non-limiting examples of materials that may be utilized to fabricate the microfluidic device may include polymer (e.g., polydimethylsiloxane (PDMS), parylene, poly(methyl methacrylate) (PMMA), negative photoresist SU-8 etc.), silicon, silica, silicon-based material (e.g., silicon nitride), metal (e.g., titanium), glass, quartz, ceramic, paper, hydrogel, thermosets, elastomers, plastics, thermoplastics, or combinations thereof. Materials may be opaque, transparent, or translucent. Materials used to fabricate the device may be of any size. For example, a 1-inch, 2-inch, 4-inch, 6-inch, 8-inch, 10-inch, or 12-inch silicon wafer may be used.

For device fabrication, various processing steps may comprise, for example, deposition, removal, patterning, and modification of device properties. Deposition may comprise any process that grows, coats, or otherwise transfers a material onto the wafer. Exemplary technologies may include physical vapor deposition (PVD), chemical vapor deposition (CVD), electrochemical deposition (ECD), molecular beam epitaxy (MBE), atomic layer deposition (ALD), or combinations thereof. Removal may comprise any process that removes material from the wafer. Examples may include etch processes (either wet or dry) and chemical-mechanical planarization (CMP). Patterning is the shaping or altering of deposited materials, and is generally referred to as lithography. Exemplary procedures for patterning may comprise (i) coating the wafer with a chemical called a photoresist; (ii) exposing select portions of the wafer to short wavelength light; and (iii) washing away the exposed regions by a developer solution. After etching or other processing, the remaining photoresist is removed by plasma ashing. In some cases, the wafer is etched to produce trenches with a specified depth by deep reactive ion etching (DRIE).

In some cases, the microfluidic device may be manufactured via a "bottom-up" approach, which may comprise (i) growing silicon nanostructures onto a clean silicon surface of a silicon base segment with the other surfaces of the base segment coated with silica; (ii) oxidizing the grown silicon nanostructures; (iii) removing the silica from the distal ends of the base segment and the silicon nanostructures to expose silicon; and (iv) removing silicon from the interior of the structure to form an emitter.

In some cases, a "top-down" approach may be applied for fabricating the microfluidic device. As described herein, this approach may comprise steps of (i) etching a trench into the surface of a silicon substrate; (ii) sealing a silicon wafer onto the surface of the substrate, thus enclosing the trench to form a channel; (iii) cutting the two channel ends; (iv) oxidizing structure; (v) cutting one end of the structure to expose the silicon core structure; and (vi) removing a portion of the silicon core to form an emitter.

A fabricated device may comprise one or more substrates which may be made of the same or different materials, such a material or a combination of materials selected from metals, semiconductors and polymeric materials (e.g., plastics). In some examples, the fabricated device is formed of glass, silicon, a silicon-based material (e.g., silicon nitride or silica), a metal, paper, hydrogel, thermoset, elastomer, or thermoplastic. For example, the microfluidic device may comprise a first substrate and a second substrate, wherein the first substrate the second substrate may be formed of different materials (e.g., silicon and silicon oxide respectively) and have one or more functional modules (e.g., fluid channels, emitter, nozzles, pumps, valves etc.) disposed there between. In some cases, the microfluidic device may comprise three substrates, wherein the first two layers may be made of a certain material and the third layer may be made of a different material. In some cases, each substrate comprised in the microfluidic device may have at least one layer. A fabricated device may comprise a single layer or multiple layers.

To establish a robust and high-quality fluidic connection to sustain high pressure for on-chip and online sample separation, a manifold may be utilized to mechanically assemble the device with capillary tubing connected to the outside flow source. The device may be sandwiched between a PEEK clamping plate and an aluminum plate, and tightly clamped by screws with O-rings in-between to prevent the fluid leakage. The top PEEK plate may have a plurality of threaded ports for Upchurch fittings to provide connections with capillary tubing. The assembly may then be fastened to a translational stage, using a screw in the aluminum plate. High voltage may be supplied to the device via the conductive aluminum plate.

Also provided herein are methods of manufacturing multiplex chips for assay multiplexing. Two approaches may be utilized to implement the multiplex chips. First, the multiplex chips may be built on silicon wafers as a whole complete piece, to facilitate simpler fabrication and lower cost. Second, the multiplex chips may be assembled using parallel 1-plex units. The approach may be used to create mass production on a large wafer and dice it into individual units (i.e., 1-plex chips). After passing QC, multiple 1-plex chips may be reconstituted to a multi-plex chip by assembly or packaging methods. This approach may allow better QC and much higher device yield, ensuring high reproducibility of inter- and intra-chip performance.

Computer Control System

Figure 6:
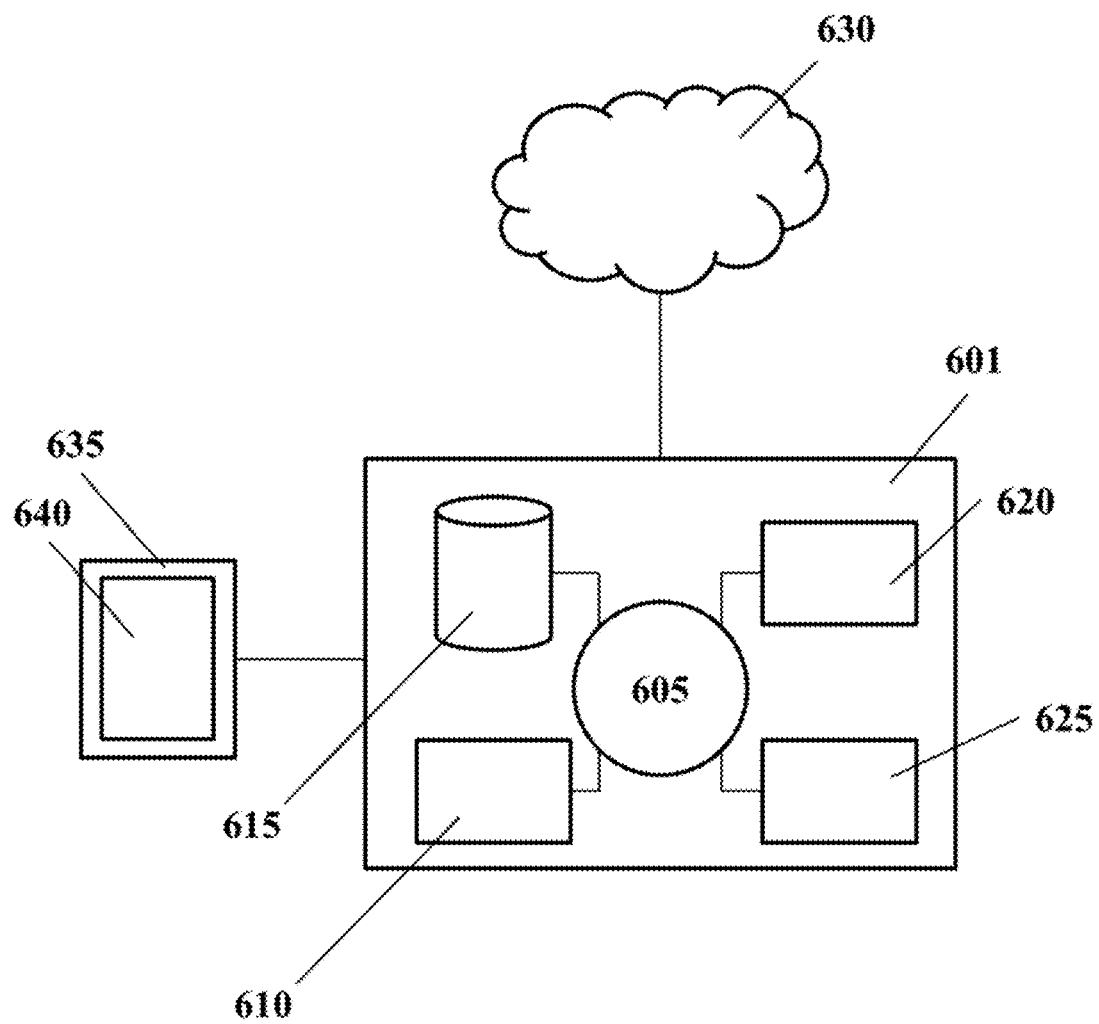
FIG. 6 shows an example computer control system that is programmed or otherwise configured to implement methods provided herein.

The present disclosure provides computer control system that is programmed to implement methods of the disclosure. FIG. 6 shows a computer system 601 that is programmed or otherwise configured to facilitate microfluidic chip operation, sample collection, preparation, processing, loading, separation, detection, and/or data analysis. The computer system 601 can regulate various aspects of sample collection, preparation, processing, loading, separation and/or detection of the present disclosure, such as, for example, loading a sample into the microfluidic device, directing the sample through one or more fluid channels in the device for sample processing, purification, enrichment and/or separation, and directing the separated target analytes from the microfluidic device to the detection module. The computer system 601 can be intergraded with the systems provided in the present disclosure.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., a physician, a nurse, a healthcare provider, a patient). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for enabling the user to instruct the computer system 601 to begin sample collection, preparation, processing, loading, separation and/or detection. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, implement the general operation of a system for sample collection, preparation, processing, loading, separation and/or detection.

Samples and Applications

Any substance may be the source of a sample. The sample may be fluid, e.g., a biological fluid. A fluidic sample may include, but is not limited to, blood or blood component (e.g., whole blood, plasma, white blood cells, red blood cells, and other cells such as immune cells), cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof. Analytes may be detected at low concentration (or quantity) in a sample, or in samples of small volumes. A sample may be solid, for example, a biological tissue. The sample may comprise normal healthy tissues. The tissues may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof. A sample may be an environmental sample (e.g. samples from agricultural fields, lakes, rivers, water reservoirs, air vents, walls, roofs, soil samples, plants, or swimming pools), or an industrial sample (e.g. samples from clean rooms, hospitals, food processing areas, food production areas, food stuffs, medical laboratories, pharmacies, or pharmaceutical compounding centers).

The sample may comprise tumors. Tumors may be benign (non-cancer) or malignant (cancer). Non-limiting examples of tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The tumors may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

The sample may comprise a mix of normal healthy tissues or tumor tissues. The tissues may be associated with various types of organs. Non-limiting examples of organs may include brain, breast, liver, lung, kidney, prostate, ovary, spleen, lymph node (including tonsil), thyroid, pancreas, heart, skeletal muscle, intestine, larynx, esophagus, stomach, or combinations thereof.

The sample may comprise a variety of cells, including, but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, and circulating cells in the human blood. In some cases, the substance comprises contents of a cell, such as, for example, the contents of a single cell or the contents of multiple cells.

A sample may be obtained from a subject at various time intervals. In some examples, samples are obtained from a subject at least every 30 seconds, 1 minute, 10 minutes, 30 minutes, 1 hour, 2 hours, 3 hours, 4 hours, 5 hours, 6 hours, 12 hours, 1 day, 1 month, 2 months, 3 months, 4 months, 5 months, 6 months, 7 months, 8 months, 9months, 10 months, 11 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 15 years, 20 years, 25 years, 30 years, or longer.

A sample may be obtained from a subject using various methods. For example, a sample may be obtained from a subject through accessing the circulatory system (e.g., intravenously or intra-arterially via a syringe, fingerstick, fingerprick, or other apparatus), collecting a secreted biological sample (e.g., saliva, sputum urine, feces, etc.), surgically (e.g., biopsy) acquiring a biological sample (e.g., intraoperative samples, post-surgical samples, etc.), swabbing (e.g., buccal swab, oropharyngeal swab), or pipetting. Such approaches may be used to obtain a biological sample of substantially low volume (e.g., less than or equal to about 5 microliters) form the subject.

Sample may be transported to a facility for analysis. The facility may be onsite or a local facility, e.g., a facility within a clinic or hospital where the sample is collected. The facility may also be an offsite or remote facility which may necessitate shipment of samples.

Samples may be stored and transported in a container. The container may be the same as the sample collection container. The container may be a transport container. The transport container may contain the sample collection container. The transport container may comprise one or more of indentations configured to accommodate one or more of sample containers. The transport container may be in communication with the sample collection container. The transport container may be empty. The transport container may comprise a secondary container. The transport container may be insulated. The secondary container may be insulated. The secondary container may be hermetically sealed. The transport container may comprise a plurality of cooling packets containing a cryogenic material (e.g., cooling packs or dry ice). The transport container may comprise a desiccant. Non-limiting examples of desiccants may include silica, activated charcoal, calcium sulfate, calcium chloride, molecular sieves, or combinations thereof. The desiccant may have a dye indicator. The dye indicator may be reactive with moisture. The transport container may comprise a temperature control module to maintain a pre-set shipping temperature. The transport container may be accommodated in an incubator. The transport container may be heated in an incubator. The transport container may be part of, or integrate with, a system for keeping cells alive. The transport container may comprise a data-logging device. The data-logging device may be programmable. The data-logging device may be configured to monitor and record the change of one or more of parameters concerning the sample during transportation. Non-limiting examples of parameters may include temperature, moisture, pressure, gas level, or a combination thereof. The data-logging device may generate a report regarding the status of the sample being shipped. The data-logging device may directly contact the transport container. The data-logging device may be attached to the transport container. The data-logging device may be separable with the transport container.

The shipping or handling time for each sample may vary depending upon, e.g., the method by which the sample is collected or prepared. The total shipping and handling time as measured from sample collection until sample processing may be less than 1 hour, less than 2 hours, less than 3 hours, less than 4 hours, less than 5 hours, less than 6 hours, less than 7 hours, less than 8 hours, less than 9 hours, less than 10 hours, less than 11 hours, less than 12 hours, less than 13 hours, less than 14 hours, less than 15 hours, less than 16 hours, less than 17 hours, less than 18 hours, less than 19 hours, less than 20 hours, less than 21 hours, less than 22 hours, less than 23 hours, or less than 24 hours. In some cases, a shipped sample may be time-stamped to provide a measure of shipping and handling times.

Quantity of total input sample that may be used in the methods provided herein may vary. In some cases, a high quantity of input sample may be used. In some cases, a low quantity of input sample may be used. In some cases, the quantity of input samples may be greater than or equal to about 1 femtogram (fg), 10 fg, 25 fg, 50 fg, 100 fg, 200 fg, 300 fg, 400 fg, 500 fg, 600 fg, 700 fg, 800 fg, 900 fg, 1 picogram (pg), 10 pg, 25 pg, 50 pg, 100 pg, 250 pg, 500 pg, 750 pg, 1 nanogram (ng), 5 ng, 10 ng, 25 ng, 50 ng, 75ng, 80 ng, 90 ng, 100 ng, 200 ng, 300 ng, 400 ng, 500 ng, 600 ng, 700 ng, 800 ng, 900 ng, 1 microgram (µg), 2 µg, 3 µg, 4 µg, 5 µg, 6 µg, 7 µg, 8 µg, 9 µg, 10 µg, 12 µg, 14 µg, 16 µg, 18 µg, 20 µg, 25 µg, 30 µg, 35 µg, 40 µg, 50 µg, 40 µg, 70 µg, 80 µg, 90 µg, 100 µg, 200 µg, 300 µg, 400 µg, 500 µg, 750 µg, 1 milligram (mg), 5 mg, 10 mg, 25mg, 50 mg, 75 mg, 100 mg or more. In some cases, the quantity of input samples may be less than or equal to about 1 gram (g), 500 mg, 250 mg, 100 mg, 50 mg, 25 mg, 10 mg, 5 mg, 1 mg, 750 µg, 500 µg, 250 µg, 125 µg, 100 µg, 75 µg, 50 µg, 40 µg, 30 µg, 25 µg, 20 µg, 19 µg, 18 µg, 17 µg, 16 µg , 15 µg, 14 µg, 13 µg, 12 µg, 11 µg, 10 µg, 9 µg, 8 µg, 7 µg, 6 µg, 5 µg, 4 µg, 3 µg, 2 µg, 1 µg, 900 ng, 800 ng, 700 ng, 600 ng, 500 ng, 400 ng, 300 ng, 200 ng, 100 ng, 75 ng, 50 ng, 25 ng, 10 ng, 5 ng, 1 ng, 750 pg, 500 pg, 250 pg, 100 pg, 50 pg, 25 pg, 10 pg, 1 pg, 750 fg, 500 fg, 250 fg, 100 fg, 50 fg, 25 fg, 10 fg or less. In some cases, the quantity of input sample falls into a range between any two of the values described herein.

The sample may comprise one or more analytes that are to be detected or identified. The one or more analytes may make up a certain percentage of the total sample input. In some cases, the one or more analytes make up a high percentage of the total input. In some cases, the one or more analytes make up a low percentage of the total input. In some cases, the one or more analytes make up less than or equal to about 100%, 95%, 90%, 80%, 70%, 60%, 50%, 40%, 30%, 20%, 10%, 5%, 1%, 0.75%, 0.5%, 0.25%, 0.1%, 0.075%, 0.05%, 0.025%, 0.01%, 0.0075%, 0.005%, 0.0025%, 0.001%, 0.00075%, 0.005%, 0.0025%, 0.001%, 0.00075%, 0.0005%, 0.00025%, 0.0001%, 0.000075%, 0.00005%, 0.000025%, 0.00001% or less of the total input. In some cases, the one or more analytes make up at least about 0.000001%, 0.000005%, 0.0000075%, 0.00001%, 0.00005%, 0.000075%, 0.0001%, 0.0005%, 0.00075%, 0.001%, 0.005%, 0.0075%, 0.01%, 0.05%, 0.075%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70%, 80%, 90%, 99%, 99.99% or more of the total input. In some cases, the percentage falls between any of the two values described herein.

A volume of the sample that can be used in the methods provided herein may vary. As provided herein, methods and systems may be adapted or configured to perform functions on a sample having either a large or a small volume. As will be appreciated, in some cases, it may be preferred to have methods or systems that may support highly-sensitive analysis on a sample of small volume. For example, in some cases, less than or equal to about 1,000 µL, 900 µL, 800 µL, 700 µL, 600 µL, 500 µL, 400 µL, 300 µL, 200 µL, 100 µL, 90 µL, 80 µL, 70 µL, 60 µL, 50 µL, 45 µL, 40 µL, 35 µL, 30 µL, 25 µL, 20 µL, 15 µL, 10 µL, 9 µL, 8 µL, 7 µL, 6 µL, 5 µL, 4 µL, 3 µL, 2 µL, 1 µL, 900 nL, 800 nL, 700 nL, 600 nL, 500 nL, 400 nL, 300 nL, 200 nL, 100 nL, 75 nL, 50 nL, 25 nL, 10 nL, 1 nL, 750 picoliter (pL), 500 pL, 250 pL, 100 pL, 75 pL, 50 pL, 25 pL, 10 pL, 5 pL, 1 pL or less of the sample is used. In some cases, the volume of input sample is between any of the two values described herein.

A variety of biological states or conditions can be identified and/or monitored by the methods and systems of the present disclosure. As discussed above and elsewhere herein, the biological state or condition includes, but not limited to, a contamination, a disease, a disorder, a non-disease condition, or therapeutic responses to different drug treatments and/or other therapies.

In some cases, the methods and systems of the present disclosure may be used for biomonitoring, which involves e.g., measuring and/or monitoring analytes in a sample (e.g., human tissues and fluids, blood and urine) of a subject. The subject may be a mammal, such as a human. The subject may be exposed to chemicals through the air, water, food, soil, dust, and consumer products. The analytes may be detected or measured in a very small amount of sample.

The biological state or condition of the subject may comprise neoplastic conditions, including, but not limited to, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic my elogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

The biological state or condition of the subject may comprise cardiovascular diseases. Examples of cardiovascular disease include, but are not limited to, coronary heart disease, ischemic heart disease, cardiomyopathy, hypertensive heart disease, pulmonary heart disease, congestive heart failure, inflammatory heart disease, valvular heart disease, cerebrovascular disease, peripheral arterial disease, congenital heart disease, rheumatic heart disease, high blood pressure, arrhythmias, atherosclerosis, cholesterol, Wolff-Parkinson-White Syndrome, long QT syndrome, angina pectoris, tachycardia, bradycardia, atrial fibrillation, ventricular fibrillation, congestive heart failure, myocardial ischemia, myocardial infarction, cardiac tamponade, myocarditis, pericarditis, arrhythmogenic night ventricular dysplasia, hypertrophic cardiomyopathy, Williams syndrome, heart valve diseases, endocarditis, bacterial, pulmonary atresia, aortic valve stenosis, Raynaud's disease, Raynaud's disease, cholesterol embolism, Wallenberg syndrome, Hippel-Lindau disease, and telangiectasis.

The biological state or condition of the subject may comprise autoimmune disorders. Examples of autoimmune disorders include, but are not limited to, inflammation, antiphospholipid syndrome, systemic lupus erythematosus, rheumatoid arthritis, autoimmune vasculitis, celiac disease, autoimmune thyroiditis, post-transfusion immunization, maternal-fetal incompatibility, transfusion reactions, immunological deficiency such IgA deficiency, common variable immunodeficiency, drug-induced lupus, diabetes mellitus, Type I diabetes, Type II diabetes, juvenile onset diabetes, juvenile rheumatoid arthritis, psoriatic arthritis, multiple sclerosis, immunodeficiency, allergies, asthma, psoriasis, atopic dermatitis, allergic contact dermatitis, chronic skin diseases, amyotrophic lateral sclerosis, chemotherapy-induced injury, graft-vs-host diseases, bone marrow transplant rejection, Ankylosing spondylitis, atopic eczema, Pemphigus, Behcet's disease, chronic fatigue syndrome fibromyalgia, chemotherapy-induced injury, myasthenia gravis, glomerulonephritis, allergic retinitis, systemic sclerosis, subacute cutaneous lupus erythematosus, cutaneous lupus erythematosus including chilblain lupus erythematosus, Sjogren's syndrome, autoimmune nephritis, autoimmune vasculitis, autoimmune hepatitis, autoimmune carditis, autoimmune encephalitis, autoimmune mediated hematological diseases, lc-SSc (limited cutaneous form of scleroderma), dc-SSc (diffused cutaneous form of scleroderma), autoimmune thyroiditis (AT), Grave's disease (GD), myasthenia gravis, multiple sclerosis (MS), ankylosing spondylitis. transplant rejection, immune aging, rheumatic/autoimmune diseases, mixed connective tissue disease, spondyloarthropathy, psoriasis, psoriatic arthritis, myositis, scleroderma, dermatomyositis, autoimmune vasculitis, mixed connective tissue disease, idiopathic thrombocytopenic purpura, Crohn's disease, human adjuvant disease, osteoarthritis, juvenile chronic arthritis, a spondyloarthropathy, an idiopathic inflammatory myopathy, systemic vasculitis, sarcoidosis, autoimmune hemolytic anemia, autoimmune thrombocytopenia, thyroiditis, immune-mediated renal disease, a demyelinating disease of the central or peripheral nervous system, idiopathic demyelinating polyneuropathy, Guillain-Barre syndrome, a chronic inflammatory demyelinating polyneuropathy, a hepatobiliary disease, infectious or autoimmune chronic active hepatitis, primary biliary cirrhosis, granulomatous hepatitis, sclerosing cholangitis, inflammatory bowel disease (including Crohn's disease (CD) and ulcerative colitis (UC)), gluten-sensitive enteropathy, Whipple's disease, an autoimmune or immune-mediated skin disease, a bullous skin disease, erythema multiforme, allergic rhinitis, atopic dermatitis, food hypersensitivity, urticaria, an immunologic disease of the lung, eosinophilic pneumonias, idiopathic pulmonary fibrosis, hypersensitivity pneumonitis, a transplantation associated disease, graft rejection or graft-versus-host-disease, psoriatic arthritis, psoriasis, dermatitis, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism, autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Sheehan's syndrome, autoimmune hepatitis, lymphoid interstitial pneumonitis (HIV), bronchiolitis obliterans (non-transplant) vs NSIP, Guillain-Barre' Syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, and amyotrophic lateral sclerosis (ALS). In some cases, the autoimmune disease is SLE, rheumatoid arthritis, or celiac's disease.

Methods and systems provided herein may be utilized for diagnosing and/or monitoring the progression and therapeutic responses of Huntington's Disease, Parkinson's Disease, Alzheimer's disease (AD) or any other neurodegenerative diseases including but not limited to Alexander's disease, Alper's disease, ataxia telangiectasia, Batten disease, bovine spongiform encephalopathy, Canavan disease, Cockayne syndrome, corticobasal degeneration, Creutzfeldt-Jakob disease, HIV-associated dementia, Kennedy's disease, Krabbe's disease, lewy body dementia, Machado-Joseph disease, multiple sclerosis, multiple system atrophy, narcolepsy, neuroborreliosis, Pelizaeus-Merzbacher Disease, peripheral neuropathy, Pick's disease, primary lateral sclerosis, prion diseases, Refsum's disease, Sandhoffs disease, Schilder's disease, subacute combined degeneration of spinal cord secondary to pernicious anaemia, schizophrenia, spinocerebellar ataxia, spinal muscular atrophy, Steele-Richardson-Olszewski disease, and tabes dorsalis.

Methods and systems provided herein may be utilized for diagnosing and/or monitoring the ionizing radiation (IR) damage to the body of a subject and the subsequent diseases arising from the radiation damage. Example biomarkers of acute and delayed radiation injury after a radiological/nuclear terrorist incident may comprise those that arise and are measurable prior to manifestation of tissue injuries, for example, one to a few days after IR exposure. They may be measurable in a non-invasive or minimally invasive way, e.g., using peripheral blood. The microfluidic chips disclosed herein may simultaneously detect cellular and molecular markers associated with IR-induced cellular and molecular changes using peripheral blood. Further, the microfluidic chips disclosed herein may diagnose and monitor the consequential diseases such as maycer as a result of IR.

EXAMPLES

Example 1

Design and Fabrication of SPE-LC-MS Microfluidic Chips

The single-plex chips are designed using the L-Edit software (v15, Tanner Research). The single-plex chip has a two-layer Si—Si structure that monolithically integrates several functional modules on the chip, including a LC column of 64 mm (length)×100 micron (width)×100 micron (depth), a trap/enrichment column of 16 mm (length)×300 micron (width)×100 micron (depth), and a SPE column of 44 mm (length)×300 micron (width)×100 micron (depth). In addition, a herringbone mixer is created between the SPE column and trap column. In order to fit a sufficient amount of herringbone grooves within the chip geometry, a convoluted path (switch-backs rather than a straight line) is used to fit them within a small footprint. The herringbone grooves are staggered periodically with a groove height of 70 micron and a channel height of 100 micron. The microfabricated emitter has nozzles with a cross-section of 25 micron×25 micron and a protruding length of 250 micron. A makeup-flow channel between the exit of the LC column and the emitter is employed to improve spray and signal stability. Through-holes are produced as the fluid inlet or outlet.

A robust manifold is built to mechanically assemble the microfluidic chip with external flow sources. Built-in frits (micro-pillar array) are designed for packing beads inside columns. The SPE, trap, and LC columns are packed with ZORBAX SB-C18 beads (5 micron, pore size of 80 Å, Agilent) by an in-house column packing station. The back-end of packed channels are sealed by fabricating sol-gel frits to prevent beads from retreating during experiments. Packed columns and sol-gel frits are examined using an Olympus IX83 microscope by infrared microscopy.

Example 2

Operation of SPE-nanoLC-MS Chips

Figure 1B:
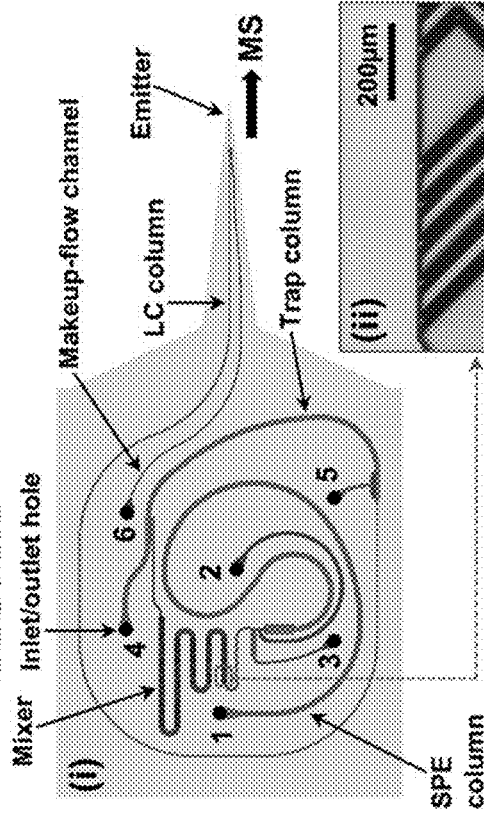

As shown in FIG. 1A(i), an example SPE-LC-MS chip comprises five functional modules, i.e., a SPE column, a herringbone mixer, a trap column, a LC column, and an emitter interfaced to a mass spectrometer for nanoelectrospray mass spectrometry. The herringbone mixer (FIG. 1A(ii)) is used for efficient solvent mixing, allowing for the titration of organic content to avoid solvent incompatibility between different columns. A makeup-flow channel between the exit of LC column and the emitter is employed to improve spray and signal stability. The chip is assembled with a custom-made manifold with screws and alignment pins (FIG. 1B) to provide high-pressure leak-free fluidic connections. In contrast to the conventional SPE-LC-MS systems that connect SPE and LC columns directly, the chip platform of the present disclosure includes an additional column (trap column) together with an on-chip mixer between the two columns for pre-concentration of target analytes after they are released from the SPE column and before the nanoLC-ESI analysis. The incorporation of such additional column enables the use of a large-volume, high-capacity SPE column for maximum capture of target analytes from the complex sample matrix, without the constraint of the potential volume mismatch between the SPE and nanoLC columns.

Figure 1C:
Figure 2:
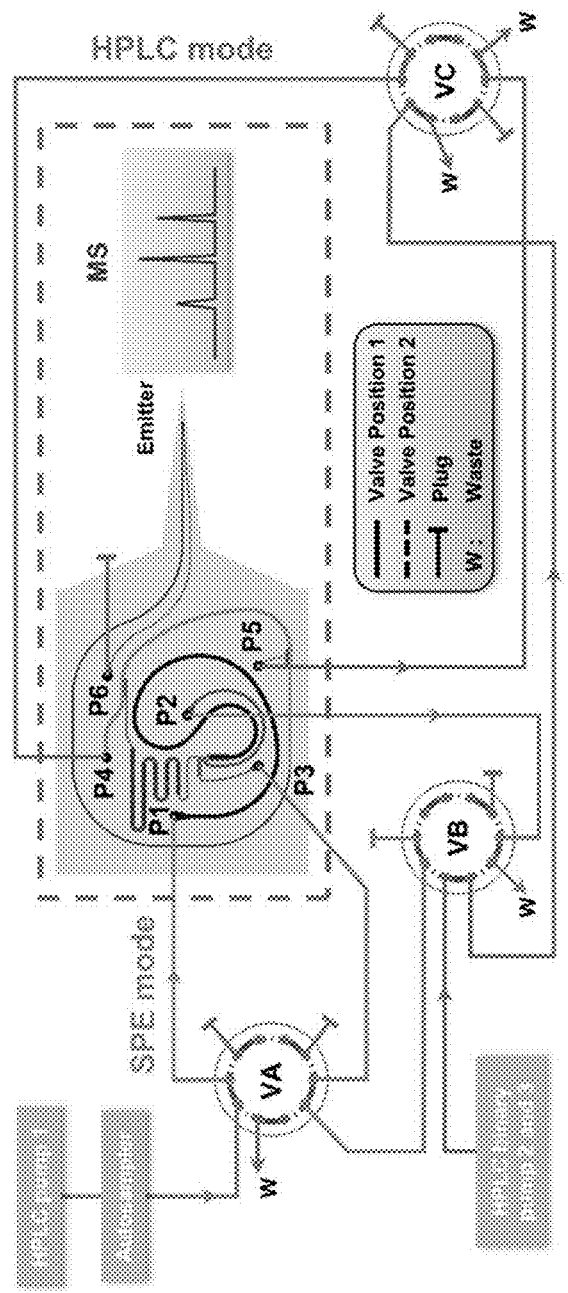
FIG. 2 shows an example system configuration and fluidic connection with external valves and pumps for chip operation of the SPE-LC-MS chip. The fluidic system includes an autosampler, three pneumatic pumps (a single HPLC pump (1) and one binary HPLC pump (2 and 3)), three 2-position switching valves (VA-VC), and six inlet/outlet ports (P1-P6) on the chip. VA, VB, and VC are 2-position switching valves. Positions shown are those during SPE sample loading. P1-P6 are inlet/outlet ports on the chip.

An example system configuration and fluidic control for the SPE-nanoLC-MS chip is shown in FIG. 2. The fluidic system includes an autosampler, three pneumatic pumps (i.e., a single HPLC pump (1) and one binary HPLC pump (2 and 3)), three 2-position switching valves (VA-VC), and six inlet/outlet ports (P1-P6) on the chip. The overall workflow includes SPE extraction, mixing, trapping, and LC-MS (FIG. 1C). In general, the workflow comprises six steps, each with a defined fluidic and valve controls at the inlet/outlet holes as illustrated in Table 1.

TABLE 1

Workflow for on-chip and online SPE-LC-MS analysis

| | | Fluidic and Valve Control | | | | |
|---|---|---|---|---|---|---|
| Steps | Method | P1 | P2 | P3 | P4 | P5 |
| 1 | Condition SPE column (20 µl LC Solvent B, 10 µl/min) | Pump1 VA-1 | Waste VB-1 | Plug VA-1 | Plug VC-1 | Waste VC-1 |
| 2 | Equilibrate SPE column (20 µl LC Solvent A, 10 µl/min) | Pump1 VA-1 | Waste VB-1 | Plug VA-1 | Plug VC-1 | Waste VC-1 |
| 3 | Load 4 µl sample onto SPE column | Pump1 VA-1 | Waste VB-1 | Plug VA-1 | Plug VC-1 | Waste VC-1 |
| 4 | Wash SPE column (20 µl LC Solvent A, 10 µl/min) | Pump1 VA-1 | Waste VB-1 | Plug VA-1 | Plug VC-1 | Waste VC-1 |
| 5 | Elute SPE column and enrich eluents on trap column (20 µl LC Solvent B, 1 µl/min, mixed with LC Solvent A at 20 µl/min) | Pump1 VA-1 | Plug VB-2 | Pump2 VA-1, VB-2 | Plug VC-1 | Waste VC-1 |
| 6 | Run HPLC gradient elution and acquire LC-MS/MS data | Plug VA-2 | Plug VB-2 | Plug VA-2, VB-2 | Pump3 VC-2 | Plug VC-2 |

As shown in Table 1, the SPE column is washed with LC solvent B and equilibrated with LC solvent A. Deproteinated plasma is then loaded onto the SPE column from P1 to P2. After washing with the LC solvent A, target analytes in the plasma are eluted from the SPE column by LC solvent B, moving towards the mixers and trap column, and exit via P5 (with P2 and P4 plugged). During the SPE elution process, another solvent stream containing LC solvent A is introduced simultaneously into P3 to titrate the eluent. This reduced the organic contents in the SPE eluent so that target analytes may be efficiently captured in the trap column. After enrichment in the trap column, LC gradients are introduced to the chip through P4 with all the other ports plugged to perform nanoflow-LC, nanoelectrospray ionization MS (nanoESI-MS). The full procedure from sample loading to completion of MS acquisition takes approximately 1 hour with SPE and nanoLC-MS each taking ~30 minutes. In order to efficiently transfer the analytes eluted from the SPE column and subsequently enrich them in the trap column, different mixing ratios between the SPE elution buffer and titration stream are investigated to achieve the optimal results on the chip.

Example 3

Preparation of Standard Samples for Validating SPE-LC-MS Microfluidic Chips

The utilities of the SPE-LC-MS chip for biomonitoring are tested by using small volumes (~1 microliter) of plasma samples containing PFCs. PFCs have been a major environment concern due to their toxicity and long half-life for bio-concentration. Despite restriction of their use in recent years, they are persistent in the environment and human body due to the chemical stability. Therefore, it is important to develop an assay that is able to perform longitudinal biomonitoring of PFCs using small volumes of samples including blood, preferably using a finger prick.

Standard stock PFCs solutions are prepared by diluting PFC standards (a list of which is shown in Table 2) in methanol in polypropylene vials. All glassware is rinsed with methanol before use. For plasma samples spiked with PFCs, frozen pooled human plasma is obtained from Innovative Research Inc. (Novi, Mich.). A 5 microliter aliquot of human plasma is thawed and mixed with 2.5 microliters of internal standards ($^{13}C_8$-PFOA and $^{13}C_8$-PFOS, 50 ng/ml), 2.5 microliters of PFC standards with desired concentration, and 20 microliters of cold acetonitrile with 0.1% formic acid. After vortexing for 2 min, the mixture is sonicated for 10 min and then centrifuged at 14,000 g for 15 min. 24 microliters of the supernatant is taken out and allowed to evaporate at room temperature until the volume is reduced to around 16 microliters. All samples are stored in polypropylene vials at minus 20 degree Celsius. Standard Reference Materials (SRMs) 1950 Metabolites in Human Plasma ordered from National Institute of Standards and Technology (NIST) are stored at minus 80 degree Celsius before use. NIST SRM 1950 is thawed at room temperature and prepared by the same procedure as pooled plasma samples for validation of the chip performance.

TABLE 2

List of PFCs with properties

| Target Analytes | Molecular Weight | Observed Precursor Ion (m/z) | Observed Product Ion (m/z) | Collision Energy (eV) | Cone Voltage (V) | Linear Range (ng/ml) | $R^2$ Value |
|---|---|---|---|---|---|---|---|
| PFHpA*# | 364.063 | 362.962 | 318.962 | 10 | 25 | 0.05-100 | N/A |
| PFHxS& | 422.097 | 398.938 | 98.988 | 10 | 25 | 0.05-100 | 0.9976 |
| $^{18}O_2$-PFHxS& | 420.097 | 402.945 | 102.945 | 10 | 25 | 0.05-100 | 0.9982 |
| PFOA*# | 414.071 | 412.963 | 368.961 | 10 | 25 | 0.05-100 | N/A |
| $^{13}C_4$-PFOA# | 418.040 | 416.973 | 371.975 | 10 | 25 | 0.05-100 | 0.9998 |
| PFNA*# | 464.078 | 462.978 | 418.970 | 10 | 25 | 0.05-100 | N/A |
| $^{13}C_5$-PFNA# | 469.040 | 467.995 | 422.990 | 10 | 25 | 0.05-100 | 0.9998 |
| PFOS& | 522.113 | 498.950 | 98.988 | 10 | 25 | 0.05-100 | 0.9996 |
| $^{13}C_4$-PFOS& | 526.082 | 502.954 | 98.988 | 10 | 25 | 0.05-100 | 0.9998 |
| PFDeA# | 514.086 | 512.972 | 468.980 | 10 | 25 | 0.05-100 | 0.9997 |
| $^{13}C_2$-PFDeA# | 516.071 | 514.980 | 469.979 | 10 | 25 | 0.05-100 | 0.9996 |
| $^{13}C_2$-PFUnA# | 566.079 | 564.990 | 519.990 | 10 | 25 | 0.05-100 | 0.9995 |
| $^{13}C_2$-PFDoA# | 616.087 | 615.000 | 570.000 | 10 | 25 | 0.05-100 | 0.9994 |
| PFOSA& | 499.146 | 497.953 | 77.978 | 10 | 25 | 0.05-100 | 0.9993 |
| Internal Standards | | | | | | | |
| $^{13}C_8$-PFOA# | 422.010 | 420.987 | 375.987 | 10 | 25 | | |
| $^{13}C_8$-PFOS& | 530.052 | 506.974 | 98.988 | 10 | 25 | | |

*Those compounds had strong background signals in our HPLC system.
Perfluoroalkylcarboxylic acids were quantified using their product ions.
&Perfluoroalkylsulfonates and perfluorooctanesulfonamides were quantified using their precursor ions.

In some cases, protein precipitation is performed before the on-chip SPE to minimize the nonspecific binding of the mostly hydrophobic PFCs to plasma proteins, thereby maximizing their extraction efficiency. For example, the number of PFOA binding sites to human serum albumin (HSA) is found to be over 6 and more than 90% of PFOA may be bound to HSA in human blood. Therefore, acetonitrile/formic acid is used to effectively suppress the interactions of PFCs with plasma proteins and make them free from protein binding for downstream SPE extraction. To reduce sample loss, PFCs are prepared in 50% methanol during the sample injection for maximum extraction and recovery.

The performance of the microfluidic chip of the present disclosure and its associated SPE-LC-MS assay using pooled human plasma and NIST SRM 1950 samples is tested (Table 3). As illustrated in the table, measured values of PFHxS, PFOS, and PFDeA by the chip of the present disclosure are strikingly consistent with the reference values provided for NIST SRM 1950.

TABLE 3

Concentration of PFCs in human blood samples

| | Human blood samples | | | |
|---|---|---|---|---|
| | NIST SRM 1950 | | Pooled plasma | Individual serum |
| Analytes | Measured Value (ng/ml) | Reference Value (ng/ml) | Measured Value (ng/ml) | National Exposure Report by CDC (ng/ml) [a] |
| PFHxS | 3.53 ± 0.38 | 3.25 ± 0.080 | 1.18 | 1.61 (1.45-1.79); 1.28 (1.14-1.43) |
| PFOS | 11.1 ± 0.36 | 10.6 ± 0.13 | 4.76 | 9.72 (8.45-11.2); 6.71 (6.24-7.20) |
| PFDeA | 0.364 ± 0.033 | 0.322 ± 0.007 | 0.279 | 0.289 (0.265-0.314); 0.209(0.189-0.230) |
| PFOSA | 0.172 ± 0.078 | N/A | 0.094 | <0.1; <0.1 |

[a] Geometric mean (95% confidence interval) of serum concentration for the U.S. population of 20 years and older (survey year 2009-2010; survey year 2011-2012), adapted from the Fourth National Report on Human Exposure to Environmental Chemicals, Updated Tables, February 2015, by Centers for Diseases Control and Prevention (CDC).

Example 4

SPE-LC-MS Analysis Using the Microfluidic Chips

The SPE run starts with conditioning a C18-packed SPE column by flowing 20 microliters of LC solvent B (95%/5% methanol/$H_2O$ with 2 mM ammonium acetate) at 10 microliters/min through the inlet port P1. The column is then equilibrated with 20 microliters of LC solvent A (5%/95% methanol/H2O with 2 mM ammonium acetate) at 10 microliters/min. Four microliters of the sample (containing 1microliters of plasma) are injected into a 20-microliter sample loop and loaded onto the SPE column, followed by washing with 20 microliters of LC solvent A at 10 microliters/min. Next, the analytes are eluted from the SPE column with LC solvent B at 1 microliter/min and transferred to the trap column by mixing it with another stream of LC solvent A through the port P3 (20 microliters/min). The passive microfluidic mixer including herringbone structures enables efficient mixing of two streams and thus prevents heterogeneous streaming of organic solvent from the SPE eluent, allowing the analytes to be enriched on the trap column efficiently. Finally the HPLC gradient elution at flow rate of 600 nl/min is run to separate the analytes that are to be analyzed by nanoESI-MS. The LC solvent A consists of 5%/95% methanol/$H_2O$ with 2 mM ammonium acetate, and solvent B consists of 95%/5% methanol/H2O with 2 mM ammonium acetate. The LC gradient starts at 10% B, which is then linearly increased to 55% B in 3 minutes, and ramped to 75% in 10 minutes. After that, it is increased to 95% B in 5 minutes and held at 95% B for 5 minutes. Finally it returns to the initial condition (10% B) in 2 minutes and is held for 5 minutes. The total time period for each SPE-LC-MS run is about one hour. Negative-ion-mode MS detection are performed on a hybrid quadrupole/orthogonal Q-TOF API US mass spectrometer (Waters Corp.). The capillary voltage and cone voltage are set to −2.4 kV and 25 V, respectively, and the collision energy is fixed at 10 eV. The nanoelectrospray process on emitters is visualized and monitored using a Waters nanoflow camera kit equipped with a MLH-10 Zoom lenses (Computar).

The raw LC-MS data are processed using MassLynx 4.0 software package provided with the Q-TOF API US instrument (Waters Corp.). Extracted ion chromatograms (EIC) for all target analytes are generated using their corresponding precursor/product ions with a mass window of 0.10 Da. The peak area ratio of each analyte relative to its corresponding isotope-labelled internal standard is used for quantification. For perfluorocarboxylate compounds, their product ions are used for quantitation, because their product ions are more abundant (3-5 times) than precursor ions under current MS settings. The abundance ratio between the product ion and precursor ion for each perfluorocarboxylate compound is found to be consistent over the wide concentration range (1-100 ng/ml). For the four perfluorosulfonates and one perfuorosulfonamide, their precursor ions are used for quantitation. The peak area ratio (defined as response RF) of each analyte to its corresponding isotope-labelled internal standard is used for quantification. Solvent composition is found to have a much larger impact on ionization efficiency of the target PFC compounds than their molecular structures. Therefore the internal standard for each compound is selected based on retention time rather than its type. $^{13}C_8$-PFOA is used for the five early eluting compounds (PFHpA, PFHxS, $^{18}O_2$-PFHxS, PFOA, and $^{13}C_4$-PFOA), while $^{13}C_8$-PFOS is used for the other compounds that eluted later in the gradient.

The calibration curves are obtained by calculating the responses for eight concentrations of PFC standards spiked in 1 microliter of pooled human plasma (0, 0.05, 0.2, 0.5, 2, 10, 30, 100 ng/ml). The limit of detection (LOD) is determined with the lowest concentration (0.05-0.2 ng/ml) in the calibration curve and defined as the signal-to-noise (S/N) ratio is equal to 3. S/N ratios are calculated by Masslynx software as the peak-to-peak values. Accuracy of the method is obtained by analyzing 1 microliter of pooled human plasma spiked with PFCs at three different concentrations (1, 5, 25 ng/ml). The PFC concentration is determined according to the calibration equation. Accuracy and precision of the method are expressed as the average value and the relative standard deviations of the ratio of the calculated concentration relative to the expected concentration for each spiking concentration. To assess the reproducibility of the method, both the inter-day and intra-day variations are measured by analyzing pooled plasma with spiking concentration of 5 ng/ml. To obtain statistical values, at least three replicates are measured. All error bars shown are standard deviations.

Because the overall sample preparation includes both protein precipitation and SPE extraction steps, the overall sample recovery of the PFCs from plasma is determined by two separate experiments. In the first experiment, 5 microliters of plasma spiked with 125 pg of each of the PFCs but without the internal standards is prepared. An aliquot (1/5)

of the sample containing 1 microliter plasma and 25 pg of each of PFCs is injected and flow through the SPE procedure until the analytes are enriched on the trap column. Then 25 pg of each internal standard is injected into the trap column using an autosampler. Although injected separately, the PFCs and the internal standards are enriched on the same trap column. Subsequently, a HPLC gradient flow is run and LC-MS/MS data are acquired. A response (RFa) is obtained for each PFCs. In the second experiment, 5 microliters of plasma without spiked PFCs or spiked internal standards are prepared. An aliquot (1/5) of the above sample containing only 1 microliter plasma is loaded to SPE column and go through the SPE procedure until the analytes are enriched on the trap column. 25 pg of each internal standard and PFC is then injected into the trap column using an autosampler and analyzed by LC-MS. Another response (RFb) is obtained from this experiment. The main difference between the two experiments is that only the PFCs in the first experiment go through the protein precipitation and SPE procedure. The overall sample recovery is determined by the ratio of RFa:RFb because the internal standards used for both experiments undergo the same procedures and the matrix effects are equivalent.

Figure 3:
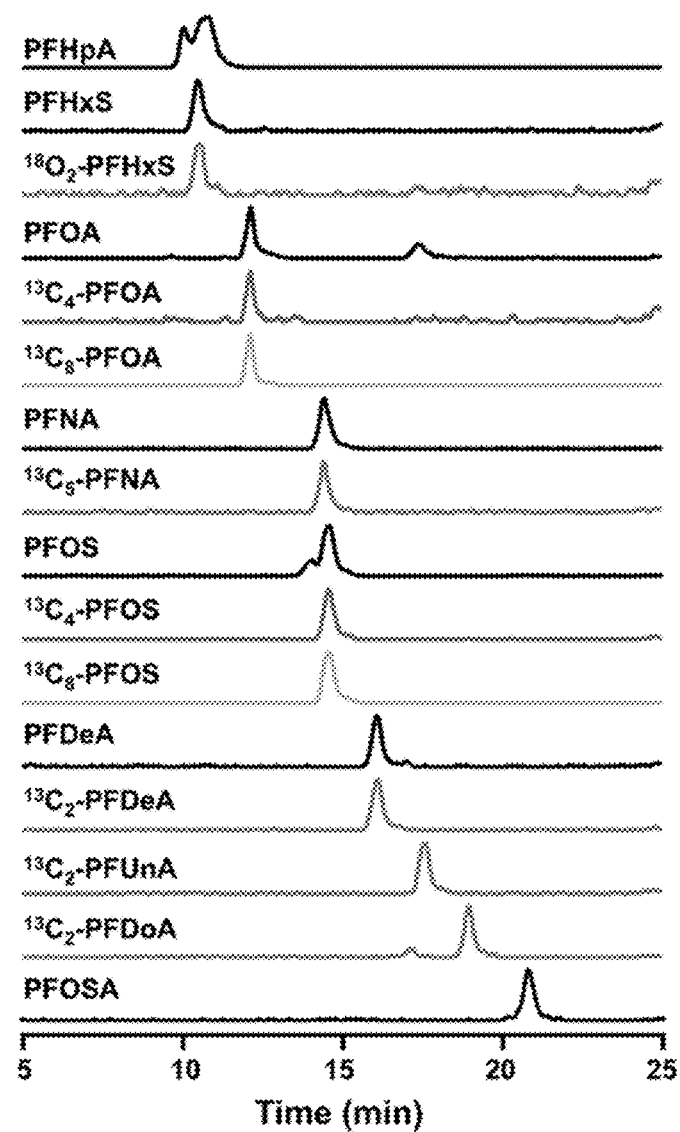
FIG. 3 shows the separation of PFCs on an example SPE-LC-MS chip. An example extracted ion chromatograms are shown for online SPE-LC-MS analysis of 1 microliter pooled human plasma spiked with PFCs of 1 pg each.

FIG. 3 shows example EICs for PFCs spiked in 1 microliter human plasma, including 1 pg of each PFC compound and 25 pg of each internal standard. The peaks for PFCs are identified and assigned according to the pair of their precursor and product ions (m/z) for each PFC compound and the corresponding retention time. The high mass accuracy of QTOF mass spectrometer simplified the compound identification by setting a narrow mass window (0.1 Da) for EIC, in contrast to typical multiple reaction monitoring (MRM) analyses using wider mass windows. A shoulder corresponding to its two chromatographic isoforms (branched vs. linear) is observed on the PFOS peak, which further confirms the high separation efficiency of the on-chip LC column of the present disclosure.

Figure 4A:
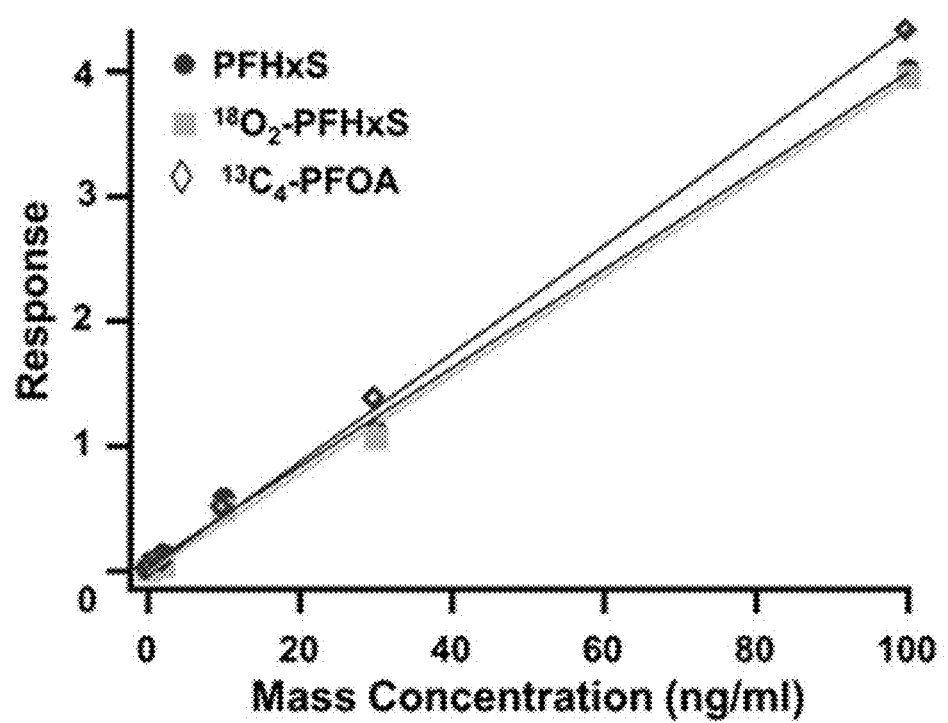
FIGS. 4A and 4B show example calibration curves for PFC compounds. The response is obtained by calculating the ratios of peak areas between analytes and the internal standards over the concentration ranges of 0-100 ng/ml.
Figure 4B:
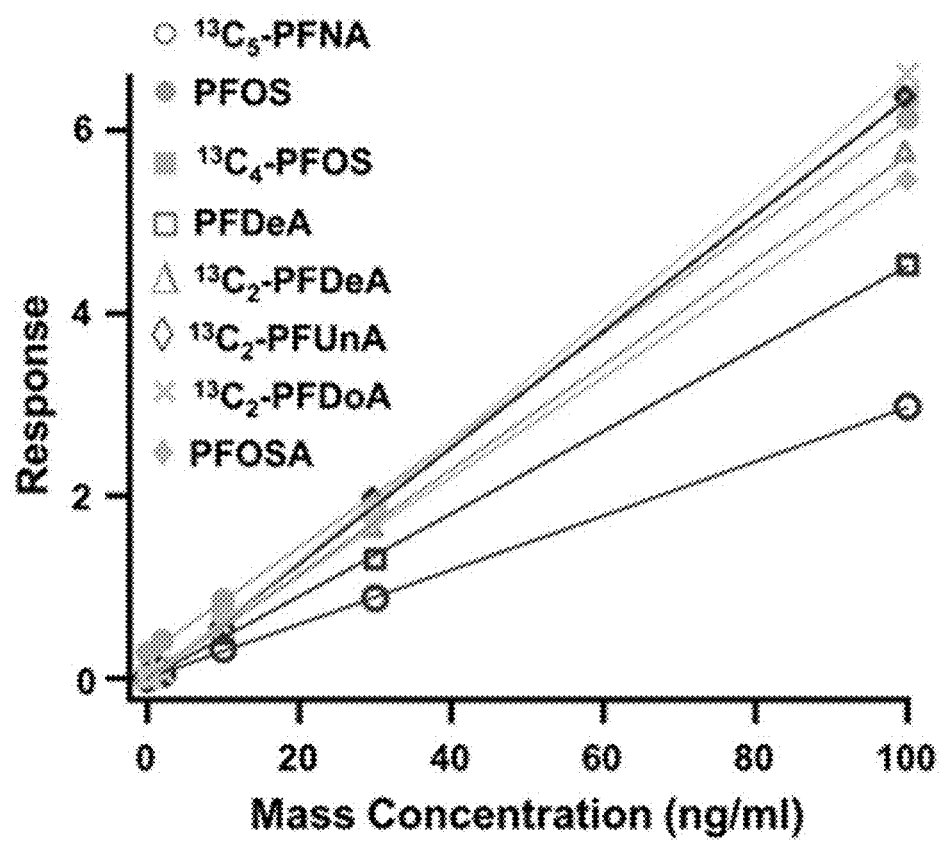

Responses (peak area ratios) for eight concentrations of analyte standards (0.05-100 ng/ml) spiked in pooled human plasma relative to their assigned isotope-labeled internal standard are calculated. The calibration curves (FIGS. 4A and 4B) exhibit excellent linearity with all correlation coefficients $R^2 > 0.99$, except PFHpA, PFOA and PFNA due to the strong background signals, which signals can be reduced by replacement of all Teflon-related tubing, fitting, and solvent filters.

Figures 5A, 5B:
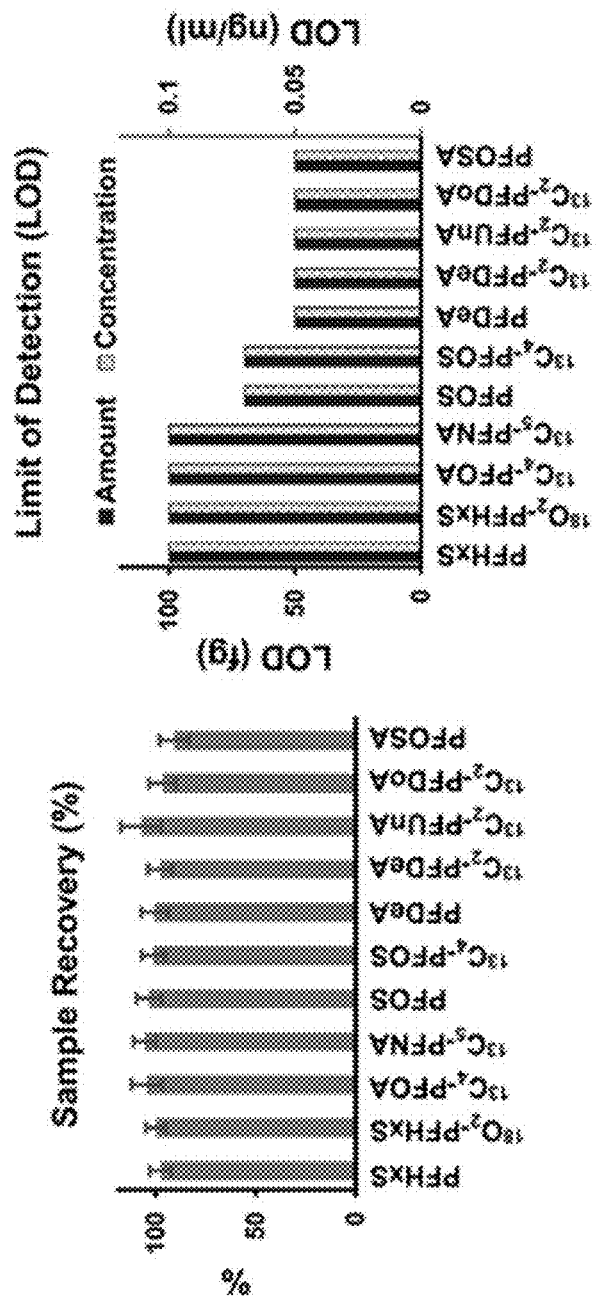
FIGS. 5A and 5B show validation of PFC analysis on an example SPE-LC-MS chip.

Sample recovery for the whole process including both the protein precipitation and SPE extraction steps is determined and high recovery (≥90.8%) is achieved for all the analytes (FIG. 5A). The accuracy, precision, reproducibility, and limit of detection (LOD) of SPE-LC-MS analysis of PFCs in human plasma using the SPE-LC-MS chip are also determined (FIG. 5B and Table 4). LOD is obtained by using the lowest concentration (0.05-0.2 ng/ml) in the calibration curve, with the signal-to-noise (S/N) ratio equal to 3.0. As shown in FIG. 5B, the LOD for PFCs obtained with the methods of the present disclosure is in the range of 0.05-0.2 ng/ml (corresponded to 50-200 fg in absolute amounts), which is significantly better than those reported in the previous study using much larger sample volumes (≥100 microliters serum) with the absolute amount of PFCs (~10 pg).

Accuracy and precision of the method are determined by replicate analyses (n≥3) of 1 microliter plasma spiked at three different concentrations (1, 5, and 25 ng/ml each). For the concentration of 5 ng/ml, inter-day and intra-day comparison is also conducted. Accuracy is defined as the average percentage of the expected amount for each concentration, and the precision is determined by calculating the relative standard deviations (RSD). As shown in Table 4, high accuracy (≥88.22%) and precision (RSD=1.47%-16.77%) are achieved. Slightly larger fluctuation at the low concentration (1 ng/ml) is probably due to the sample loss during transfer from the HPLC system to the chip. Reproducibility of the method is confirmed by the intra-day and inter-day accuracy and precision at 5 ng/ml.

TABLE 4

Accuracy and precision at the different concentrations of PFCs

| | Accuracy ± Precision (%) | | | |
| --- | --- | --- | --- | --- |
| | 5 ng/ml | | | |
| Analytes | Inter-day | Intra-day | 1 ng/ml | 25 ng/ml |
| PFHxS | 88.7 ± 3.8 | 92.2 ± 6.8 | 112 ± 15 | 102 ± 12 |
| $^{18}O_2$-PFHxS | 91.9 ± 4.4 | 95.2 ± 6.9 | 99.9 ± 10 | 95.2 ± 12 |
| $^{13}C_4$-PFOA | 97.5 ± 6.0 | 98.0 ± 5.6 | 97.2 ± 12 | 95.2 ± 3.6 |
| $^{13}C_5$-PFNA | 96.5 ± 10 | 99.7 ± 10 | 97.0 ± 6.2 | 103 ± 6.7 |
| PFOS | 107 ± 2.5 | 106 ± 7.8 | 107 ± 11 | 97.5 ± 4.9 |
| $^{13}C_4$-PFOS | 96.6 ± 1.5 | 100 ± 6.8 | 95.9 ± 5.7 | 103 ± 4.6 |
| PFDeA | 93.7 ± 8.7 | 95.8 ± 9.6 | 106 ± 5.1 | 107 ± 8.9 |
| $^{13}C_2$-PFDeA | 90.8 ± 8.4 | 94.9 ± 9.7 | 101 ± 4.7 | 104 ± 7.3 |
| $^{13}C_2$-PFUnA | 102 ± 8.6 | 96.6 ± 8.5 | 101 ± 2.6 | 97.1 ± 8.4 |
| $^{13}C_2$-PFDoA | 93.0 ± 4.3 | 96.1 ± 3.7 | 104 ± 12 | 97.0 ± 4.8 |
| PFOSA | 88.2 ± 14.9 | 91.8 ± 13 | 103 ± 17 | 119 ± 14 |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing or analyzing a biological sample of a subject, comprising:
(a) providing a microfluidic device comprising (i) a first fluid channel including a first separation medium that is adapted to extract a plurality of analytes from said biological sample; (ii) a second fluid channel in fluid communication with said first fluid channel, wherein said second fluid channel includes a second separation medium that is adapted to separate said plurality of analytes extracted in said first separation medium into subsets of analytes along said second fluid channel; (iii) a third fluid channel between and in fluid communication with said first fluid channel and said second fluid channel, wherein said third fluid channel is adapted to facilitate mixing of said plurality of analytes from said first fluid channel with a solvent, wherein said third fluid channel includes a barrier structure, and wherein a cross-section of said barrier structure is less than a height of said third fluid channel, and (iv) at least one emitter in fluid communication with said second fluid channel, wherein said at least one emitter comprises at least one nozzle that is operatively coupled to a detector, which detector is adapted to generate signals that are indicative of each of said subsets of analytes;

(b) directing said biological sample to said first fluid channel to extract said plurality of analytes from said biological sample, wherein said plurality of analytes extracted in said first fluid channel are mixed with said solvent in said third fluid channel;

(c) directing said plurality of analytes extracted in said first fluid channel and mixed with said solvent in said third fluid channel to said second fluid channel to separate said plurality of analytes into said subsets of analytes along said second fluid channel; and (d) directing said subsets of analytes from said second fluid channel to said at least one nozzle of said at least one emitter to said detector, wherein said detector generates signals upon exposure to said subsets of analytes, which signals are indicative of a presence of each of said subsets of analytes in said biological sample.

2. The method of claim 1, wherein said barrier structure comprises periodic structures.

3. The method of claim 1, wherein said barrier structure comprises staggered grooves.

4. The method of claim 1, further comprising identifying a biological state or condition of said subject based on said presence of each of said subsets of analytes in said biological sample, and wherein said biological state or condition is selected from the group consisting of a disease, a disorder, a non-disease condition, and a therapeutic response to drug treatments or other therapies.

5. The method of claim 4, further comprising detecting a presence of said subsets of analytes at multiple time points to monitor a progression of said biological state or condition in said subject.

6. The method of claim 1, wherein said plurality of analytes comprises perfluorinated compounds (PFCs) and other environmental toxins.

7. The method of claim 1, wherein said biological sample has a volume less than or equal to about 50 microliters.

8. The method of claim 1, wherein (b)-(d) are performed in a time period that is less than or equal to 2 hours.

9. The method of claim 1, wherein said subsets of analytes are detected at a specificity of at least about 80% or at a sensitivity of at least about 80%.

10. The method of claim 1, wherein said subsets of analytes are detected at a detection limit of less than or equal to about 1 nanogram/milliliter (ng/mL).

11. The method of claim 1, wherein said plurality of analytes comprises lipids, glycans, proteins, peptides, or nucleic acids.

12. The method of claim 1, further comprising generating an electronic report that is indicative of said presence of each of said subsets of analytes in said biological sample.

13. The method of claim 12, further comprising providing said electronic report for display on a user interface of an electronic device of a user.

14. The method of claim 1, further comprising determining a concentration or relative amount of each of said subsets of analytes in said biological sample.

15. The method of claim 14, wherein said concentration or relative amount of each of said subsets of analytes is associated with a biological state or condition of said subject.

16. A system for processing or analyzing a biological sample of a subject, comprising:

a microfluidic device comprising (i) a first fluid channel including a first separation medium that is adapted to extract a plurality of analytes from said biological sample; (ii) a second fluid channel in fluid communication with said first fluid channel, wherein said second fluid channel includes a second separation medium that is adapted to separate said plurality of analytes extracted in said first separation medium into subsets of analytes along said second fluid channel; (iii) a third fluid channel between and in fluid communication with said first fluid channel and said second fluid channel, wherein said third fluid channel is adapted to facilitate mixing of said plurality of analytes from said first fluid channel with a solvent, wherein said third fluid channel includes a barrier structure, and wherein a cross-section of said barrier structure is less than a height of said third fluid channel, and (iv) at least one emitter in fluid communication with said second fluid channel, wherein said at least one emitter comprises at least one nozzle;

a detector operatively coupled to said at least one emitter, wherein said detector is adapted to generate signals that are indicative of each of said subsets of analytes; and one or more computer processors operatively coupled to said microfluidic device, wherein said one or more computer processors are individually or collectively programmed to (1) direct said biological sample to said first fluid channel to extract said plurality of analytes from said biological sample, wherein said plurality of analytes extracted in said first fluid channel are mixed with said solvent in said third fluid channel; (2) direct said plurality of analytes extracted in said first fluid channel and mixed with said solvent in said third fluid channel to said second fluid channel to separate said plurality of analytes extracted in said first separation channel into said subsets of analytes along said second fluid channel; and (3) direct said subsets of analytes from said second fluid channel to said at least one nozzle of said at least one emitter to said detector, wherein said detector generates signals upon exposure to said subsets of analytes, which signals are indicative of a presence of each of said subsets of analytes in said biological sample.

17. The system of claim 16, wherein said barrier structure comprises periodic structures.

18. The system of claim 16, wherein said barrier structure comprises staggered grooves.

19. The system of claim 16, wherein said at least one nozzle extends from a base tube that is in fluid communication with said second fluid channel, wherein said base tube has a larger cross-sectional dimension than said at least one nozzle.

20. The system of claim 19, wherein said at least one nozzle has a cross-sectional dimension that is less than or equal to about 50 micrometers.

21. The system of claim 16, wherein said first separation medium and said second separation medium comprise beads or monolithic porous structures.

22. The system of claim 21, wherein a bead of said beads has a cross-sectional dimension from about 1 micrometer to 50 micrometers.

23. The system of claim 21, wherein a bead of said beads comprises a plurality of pores.

24. The system of claim 16, wherein said first fluid channel is configured to perform solid-phase extraction (SPE) on said biological sample.

* * * * *